United States Patent
Whiteker et al.

(10) Patent No.: US 10,358,423 B2
(45) Date of Patent: Jul. 23, 2019

(54) PROCESSES FOR THE PREPARATION OF 4-ALKOXY-3-(ACYL OR ALKYL)OXYPICOLINAMDES

(71) Applicant: Dow AgroSciences LLC, Indianapolis, IN (US)

(72) Inventors: Gregory T. Whiteker, Carmel, IN (US); Nakyen Choy, Carmel, IN (US); Peter Borromeo, Fishers, IN (US); Nicholas R. Babij, Indianapolis, IN (US); Gary Roth, Midland, MI (US); Patrick S. Hanley, Midland, MI (US); Matthias S. Ober, Midland, MI (US); Tina Staton, Midland, MI (US); Daniel I. Knueppel, Zionsville, IN (US); Grant Von Wald, Midland, MI (US); Nicole Hough, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 16/035,738

(22) Filed: Jul. 16, 2018

(65) Prior Publication Data

US 2018/0319750 A1 Nov. 8, 2018

Related U.S. Application Data

(62) Division of application No. 15/642,653, filed on Jul. 6, 2017, now Pat. No. 10,040,764.

(60) Provisional application No. 62/456,874, filed on Feb. 9, 2017, provisional application No. 62/359,288, filed on Jul. 7, 2016, provisional application No. 62/359,290, filed on Jul. 7, 2016.

(51) Int. Cl.
*C07C 227/18* (2006.01)
*C07C 229/08* (2006.01)
*C07C 269/06* (2006.01)
*C07C 271/22* (2006.01)
*C07D 213/81* (2006.01)

(52) U.S. Cl.
CPC .......... *C07D 213/81* (2013.01); *C07C 227/18* (2013.01); *C07C 229/08* (2013.01); *C07C 269/06* (2013.01); *C07C 271/22* (2013.01)

(58) Field of Classification Search
None
See application file for complete search history.

(56) References Cited

U.S. PATENT DOCUMENTS

| | | |
|---|---|---|
| 4,628,120 A | 12/1986 | Tsuchihashi |
| 4,859,639 A | 8/1989 | Batt |
| 2016/0264550 A2 | 9/2016 | Bindl |

FOREIGN PATENT DOCUMENTS

| | | | |
|---|---|---|---|
| WO | WO2004080988 A1 | 9/2004 | |
| WO | WO 2016109257 A1 * | 7/2016 | ............. A01N 37/44 |

OTHER PUBLICATIONS

Chemical Society Reviews 1998, 27, 395.
Eur. J. Org. Chem. 2005, 1082.
Tetrahedron: Asymmetry, 1990, 1, 199.
J. Am. Chem. Soc. 1990, 112, 3949.
Synthesis 2003, 1, 141.
Tetrahedron, 1993, 49, 1535.

* cited by examiner

*Primary Examiner* — Zinna Northington Davis

(57) ABSTRACT

A fungicidal 4-methoxy-3-acetyloxypicolinamide may be conveniently prepared in processes that include the coupling together of 4-methoxy-3-acetyloxypicolinic acid or 4-methoxy-3-hydroxypicolinic acid with a key 2-aminopropanoate ester derived from a 1,1-bis(4-fluorophenyl)propane-1,2-diol.

15 Claims, No Drawings

PROCESSES FOR THE PREPARATION OF 4-ALKOXY-3-(ACYL OR ALKYL)OXYPICOLINAMDES

CROSS-REFERENCE TO RELATED APPLICATIONS

This application is a divisional of U.S. patent application Ser. No. 15/642,653, filed on Jul. 6, 2017, which claims priority to U.S. Provisional Patent Application Nos. 62/359,288 and 62/359,290 filed Jul. 7, 2016; and U.S. Provisional Patent Application No. 62/456,874 filed on Feb. 9, 2017, the disclosures of which are all herein incorporated by reference in their entirety.

FIELD

The present disclosure concerns processes for the preparation of 4-alkoxy-3-(acyl or alkyl)oxypicolinamides. More particularly, the present disclosure concerns a process for the preparation of 4-methoxy-3-(acetyl or acetyloxymethyl) oxypicolinamides from 4-methoxy-3-hydroxypicolinic acids or 4-methoxy-3-acetyloxypicolinic acids.

BACKGROUND

U.S. patent application Ser. Nos. 15/036,314 and 15/036,316 describes inter alia certain heterocyclic aromatic amide compounds of general Formula

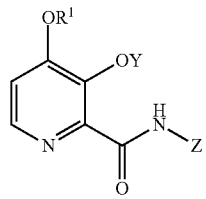

and their use as fungicides. It would be useful to have an efficient and scalable process route to these heterocyclic aromatic amide compounds from inexpensive raw materials.

SUMMARY

The present disclosure concerns processes for the preparation of the 4-methoxy-3-(acetyl or acetyloxymethyl) oxypicolinamides of Formula A

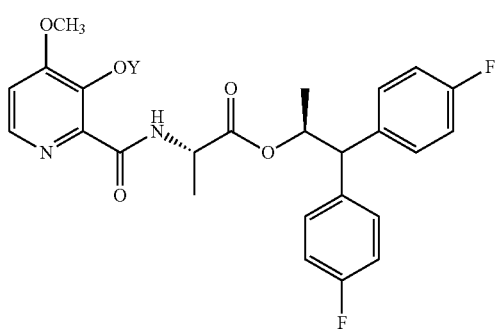

wherein Y is $CH_3CO$ or $CH_3COOCH_2$;

from the compounds of Formulas B or D

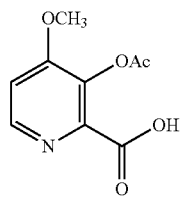

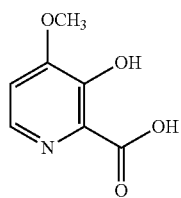

The compound of Formula A, wherein Y is $CH_3CO$, may be prepared in a process that comprises the following steps:

a) creating a first mixture containing the compound of Formula B, an acylating agent or a chlorinating agent, and a base;

b) adding the compound of Formula C

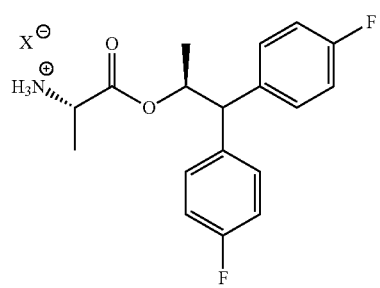

wherein X is Cl, Br, $HSO_4$, $H_2PO_4$ or $CH_3SO_3$;

to the first mixture to form a second mixture; and c) isolating the compound of Formula A from the second mixture, wherein Y is acetyl (i.e., $CH_3CO$).

The compound of Formula A, wherein Y is $CH_3CO$ or $CH_3COOCH_2$, may be prepared in a process that comprises the following steps:

a) creating a first mixture containing the compound of Formula D,

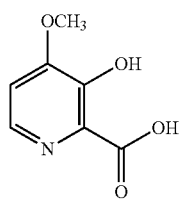

an acylating agent, and a base;

b) adding the compound of Formula C

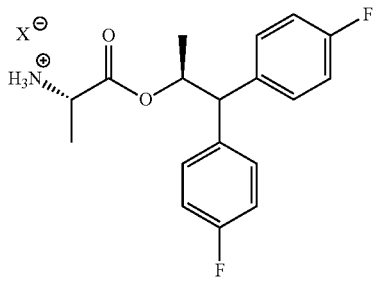

wherein X is Cl, Br, HSO$_4$, H$_2$PO$_4$ or CH$_3$SO$_3$;
to the first mixture to form a second mixture;

c) isolating the compound of Formula E from the second mixture;

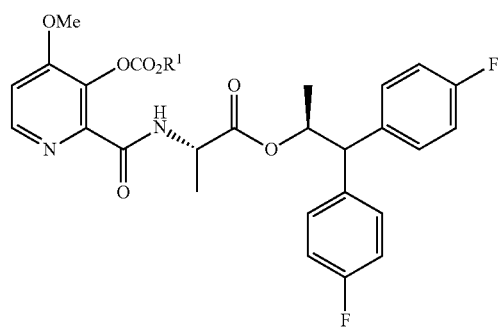

wherein R$^1$ is a C$_1$-C$_4$ alkyl or CH$_2$Ph;

d) creating a third mixture containing the compound of Formula E, an alkali metal base and water;

e) isolating the compound of Formula F from the third mixture;

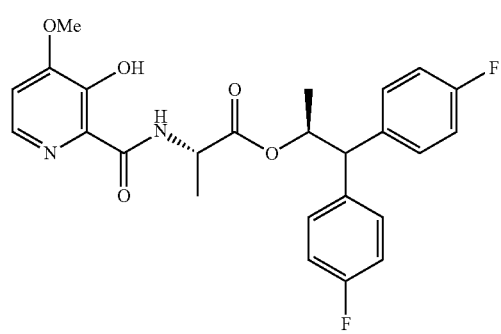

f) creating a fourth mixture containing the compound of Formula F, an acetylating agent or an alkylating agent, and a second base; and g) isolating the compound of Formula A from the fourth mixture

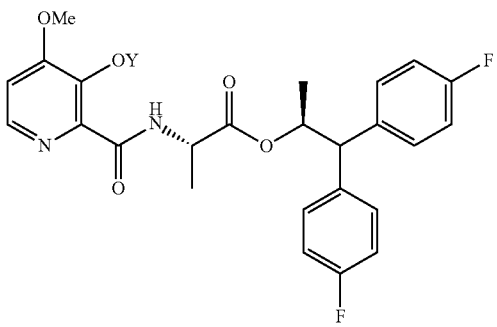

wherein Y is CH$_3$CO or CH$_3$COOCH$_2$.

The compound of Formula C

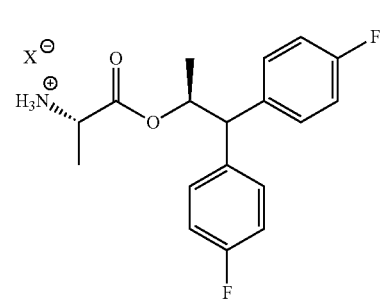

wherein X is Cl, Br, HSO$_4$, H$_2$PO$_4$ or CH$_3$SO$_3$;

may be prepared in a process that comprises the following steps:

a) creating a first mixture containing the compound of Formula G,

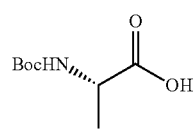

an acylating agent and a base;

b) adding the compound of Formula H

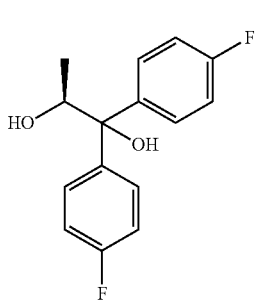

to the first mixture to form a second mixture;

c) isolating the compound of Formula I

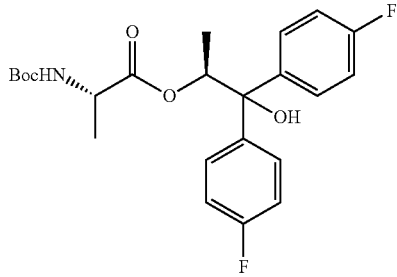

I from the second mixture;

d) creating a third mixture containing the compound of Formula I, an acid and a reducing agent;

e) isolating the compound of Formula J from the third mixture;

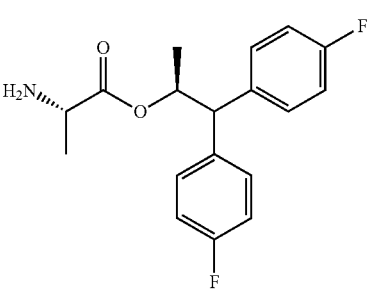

J f) creating a fourth mixture containing the compound of Formula J and a strong acid;

wherein the strong acid is HCl, HBr, $H_2SO_4$, $H_3PO_4$ or $CH_3SO_3H$;

and g) isolating the compound of Formula C from the fourth mixture.

The compound of Formula C may also be prepared in a process that comprises the following steps:

a) creating a first mixture containing the compound of Formula H, a reducing agent and an acid;

b) isolating the compound of Formula K from the first mixture;

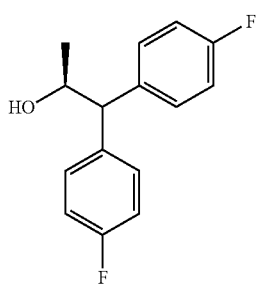

K c) creating a second mixture containing the compound of Formula G,

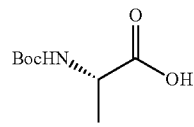

G an acylating agent and a base;

d) adding the compound of Formula K to the second mixture to form a third mixture;

e) isolating the compound of Formula L from the third mixture;

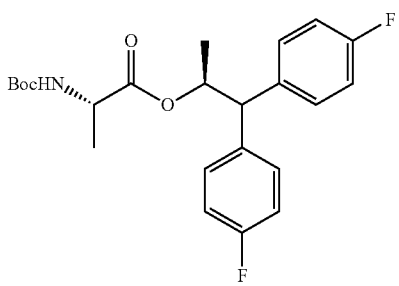

L f) creating a fourth mixture containing the compound of Formula L and a strong acid;

wherein the strong acid is HCl, HBr, $H_2SO_4$, $H_3PO_4$ or $CH_3SO_3H$;

and g) isolating the compound of Formula C from the fourth mixture.

Another aspect of the present disclosure are the novel intermediates produced in the present process, viz., the compounds:

a)

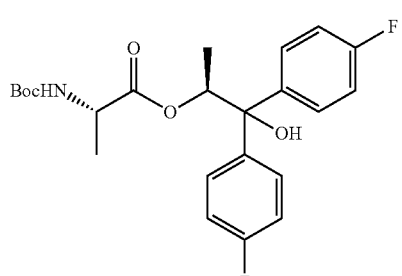

I b)

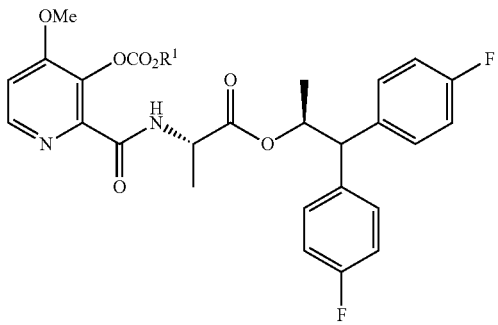

E wherein $R_1$ is a $C_1$-$C_4$ alkyl or $PhCH_2$;

c)

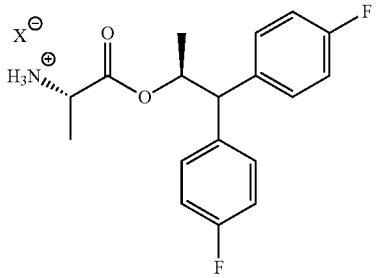

wherein X is Cl, Br, $HSO_4$, $H_2PO_4$ or $CH_3SO_3$; and

DETAILED DESCRIPTION

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "acyl", as used herein, refers to an RCO moiety (i.e., RC(O)—) which includes within its scope wherein R is a straight chain or branched chain alkyl containing from one to six carbon atoms. Specific acyl groups described herein include, for example, $CH_3CO$ (i.e., an acetyl group) and $CH_3COOCH_2$ (i.e., an acetyloxymethyl group).

The terms "isolate," "isolating," or "isolation" as used herein mean to partially or completely remove or separate the desired product from the other components of a finished chemical process mixture using standard methods such as, but not limited to, filtration, extraction, distillation, crystallization, centrifugation, trituration, liquid-liquid phase separation or other methods known to those of ordinary skill in the art. The isolated product may have a purity that ranges from <50% to >50%, and may be purified to a higher purity level using standard purification methods. The isolated product may also be used in a subsequent process step with or without purification.

In the processes described herein the picolinamide of Formula A, wherein Y is $CH_3CO$, may be prepared by coupling 4-methoxy-3-acetyloxypicolinic acid with the 2-aminopropanoate ester portion of the target molecule. Alternatively, picolinamides of Formula A, wherein Y is $CH_3CO$ or $CH_3COOCH_2$, may be prepared by a process using 4-methoxy-3-hydroxypicolinic acid in the described coupling reaction followed by addition of the Y group at the end of the process sequence.

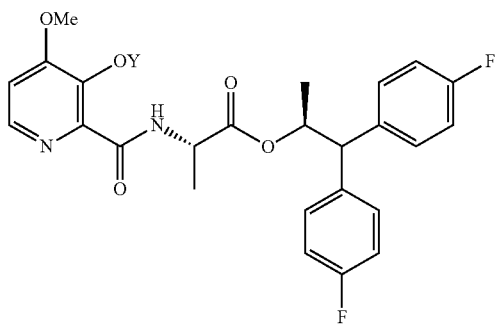

wherein Y is $CH_3CO$ or $CH_3COOCH_2$.

A. Preparation of Compound of Formula A

The compound of Formula A, wherein Y is $CH_3CO$, may be prepared directly from the compound of Formula B in the process shown in Scheme I. Picolinic acid B is first activated for coupling by converting it into (a) the corresponding mixed anhydride using an alkyl or benzyl chloroformate, or an acid chloride, and a base, or (b) the acid chloride using oxalyl chloride or thionyl chloride and a base. The resulting derivative of picolinic acid B, in the form of a mixed anhydride or an acid chloride, can be treated with the amine salt of Formula C, wherein X is Cl, Br, $HSO_4$, $H_2PO_4$ or $CH_3SO_3$, to provide the desired picolinamide of Formula A (Y is $CH_3CO$). The compound of Formula A may be isolated by employing standard isolation and purification techniques. Suitable solvents for this process may include dichloromethane (DCM), 1,2-dichloroethane (DCE), isopropyl acetate, tetrahydrofuran (THF), 2-MeTHF, and acetonitrile (ACN).

Scheme I

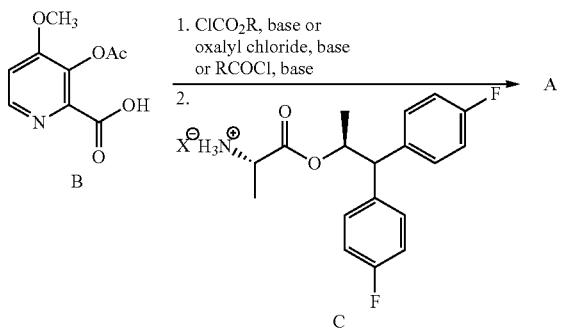

Suitable chloroformate esters (i.e., $ClCO_2R$) for use in the process may include those wherein R is a $C_1$-$C_4$ alkyl or a benzyl. Suitable acid chlorides (i.e., RCOCl) for use in the process may include those wherein R is a $C_1$-$C_4$ alkyl. Suitable bases for use in the process may include one or more of triethylamine (TEA), diisopropylethylamine (DIPEA), pyridine and potassium carbonate. At least 1, at least 2, or at least 3 molar equivalents of the base may be used in this process.

In one embodiment, the process shown in Scheme I can be conducted by using a sulfonating compound in place of the alkyl or benzyl chloroformate, or the acid chloride, to prepare the compound of Formula A. In such a process the compound of Formula B is contacted with the sulfonating compound of Formula B1, wherein $R^1$ is a $C_1$-$C_4$ alkyl and Z is Cl or Br, and a base to form the mixed sulfonic-carboxylic anhydride of Formula B2. Anhydride B2 can then be treated with the amine salt of Formula C, wherein X is Cl, Br, $HSO_4$, $H_2PO_4$ or $CH_3SO_3$, or the amine of Formula J to provide the desired picolinamide of Formula A (Y is $CH_3CO$).

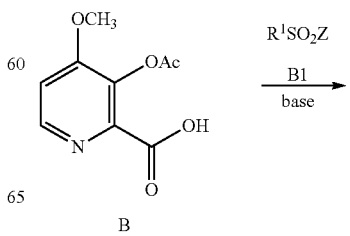

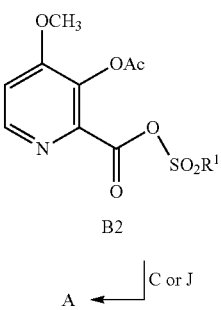

The compound of Formula A may also be prepared from the compound of Formula D in the process shown in Scheme II. Picolinic acid D is first converted into the compound of Formula D1, which is not isolated, using at least about 2 equivalents of an alkyl or benzyl chloroformate of the Formula ClCO$_2$R, wherein R is a C$_1$-C$_4$ alkyl or a benzyl, and at least about 3 equivalents of a base. The reaction mixture containing compound D1 may then be combined with the compound of Formula C to produce picolinamide E. Suitable bases such as, for example, TEA, DIPEA or similar trialkylamine bases, may be used in these reactions. Treatment of Compound E with an alkali metal base, such as LiOH, NaOH, KOH, or mixtures thereof, in the presence of water and, optionally a co-solvent, such as, for example, tetrahydrofuran (THF), 2-tetrahydrofuran (2-MeTHF), DME, dioxane, ACN or a C$_1$-C$_4$ alcohol, may provide the compound of Formula F. Acetylation of Compound F with acetic anhydride, acetyl chloride or other acetylating agents commonly used in the art and with the use of a base, or using Schotten-Baumann reaction conditions, may provide the compound of Formula A wherein Y is CH$_3$CO. Alkylation of Compound F with CH$_3$COOCH$_2$Br and a base may provide the compound of Formula A wherein Y is CH$_3$COOCH$_2$. Bases useful in these reactions may be selected from at least one of pyridine, TEA, and DIPEA. The

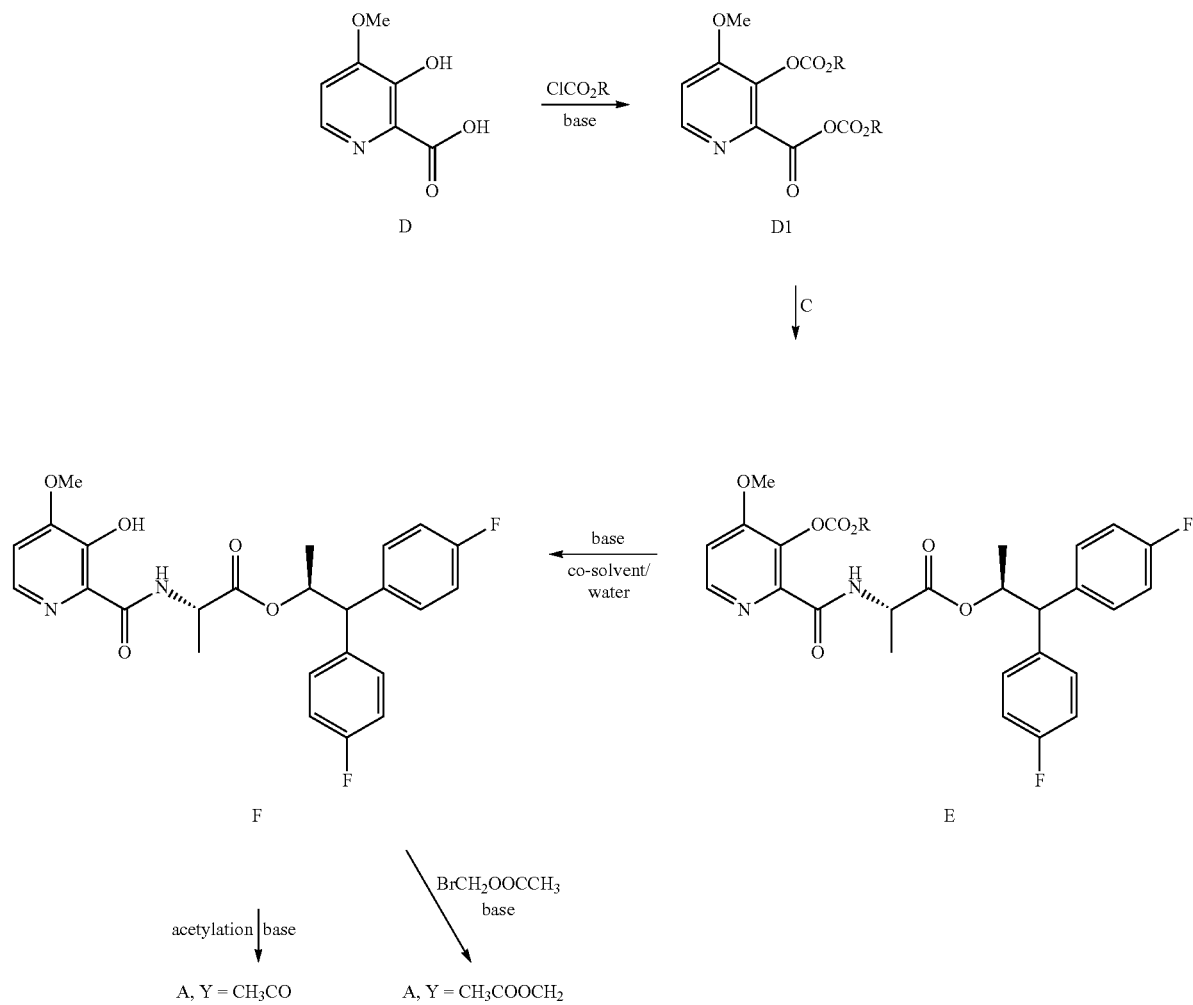

compounds of Formulas A, E and F may be isolated by employing standard isolation and purification techniques.

In the hydrolysis reaction that converts compound E to compound F in Scheme II, the compound of Formula E1 under certain conditions may be isolated as an intermediate in that reaction.

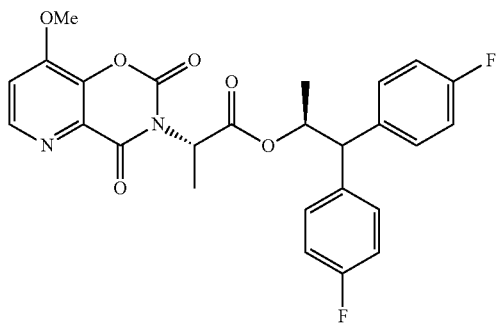

E1

In some embodiments, the picolinamide of Formula A, wherein Y is CH₃CO or CH₃COOCH₂, may be prepared by a process using the amine of Formula J in place of the amine salt of Formula C.

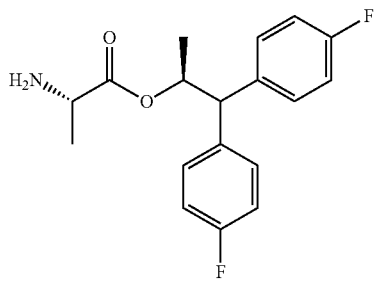

J

B. Preparation of the Compound of Formula C

The compound of Formula C may be prepared by two different processes with both starting from the diol compound of Formula H. In the first of the two processes, shown in Scheme III, the diol compound H may be coupled with the BOC-L-alanine compound G to produce the compound of Formula I. The coupling reaction may be conducted by utilizing the mixed anhydride derivative of compound G, which may be prepared by treating G with an acid chloride of formula RCOCl, wherein R is a $C_1$-$C_4$ alkyl, a base and DMAP (4-(dimethylamino)pyridine). Suitable solvents for this reaction may include one or more of DCM, DCE, THF, 2-MeTHF and ACN and suitable bases may include one or more of TEA, DIPEA, and pyridine.

Scheme III

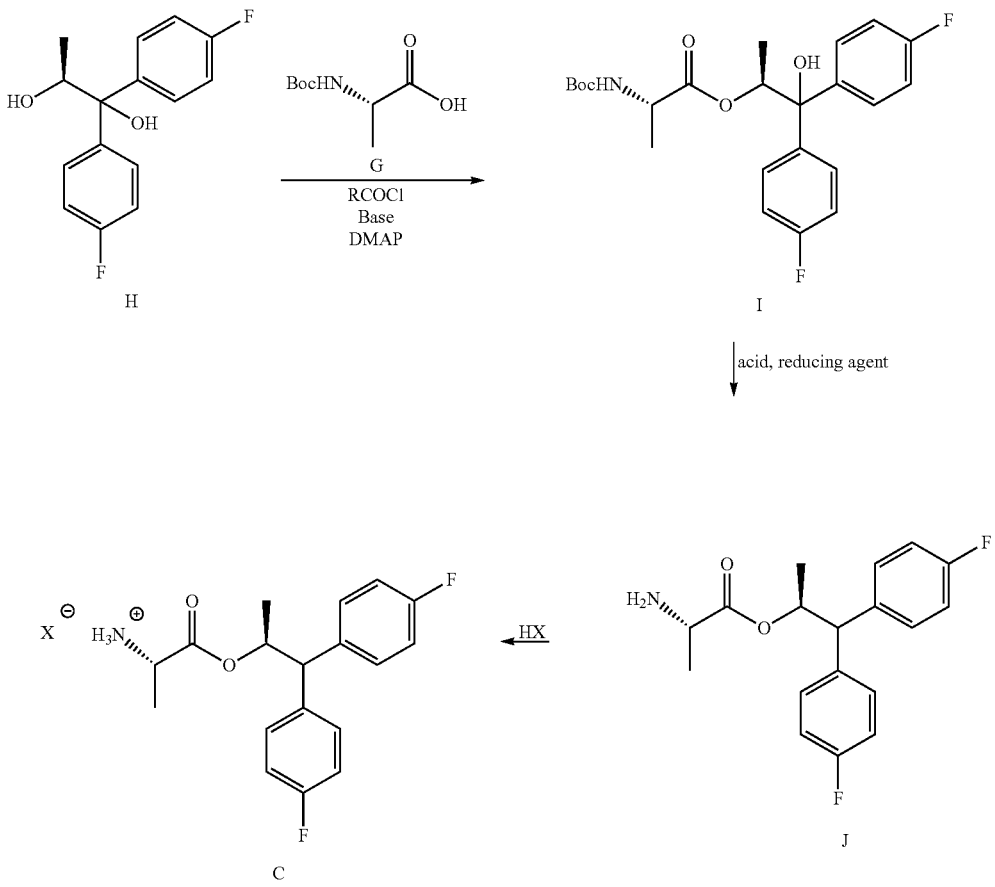

In the second step of the process shown in Scheme III, the tertiary hydroxyl group and the BOC group in the compound of Formula I are removed by use of a reducing agent combined with an acid. Suitable reducing agents for this transformation may include borohydride reagents such as, but not limited to, sodium borohydride and sodium triacetoxyborohydride, and organosilicon hydrides such as, for example, triethylsilane, poly(methylhydrosiloxane) (PMHS) and 1,1,3,3-tetramethyldisiloxane (TMDS). Suitable acids for use with the reducing agents may include, but are not limited to, trifluoroacetic acid and methanesulfonic acid. Finally, compound J may be converted into the amine salt compound of Formula C by treatment with strong acid HX utilizing anhydrous conditions, wherein HX may be selected from HCl, HBr, $H_2SO_4$, $H_3PO_4$ or $CH_3SO_3H$.

The second process for the preparation of the compound of Formula C is shown in Scheme IV. The diol compound of Formula H may be treated with an acid and a reducing agent to produce the alcohol of Formula K. Suitable reducing agents for this transformation include organosilicon hydrides such as, for example, triethylsilane, poly(methylhydrosiloxane) (PMHS) and 1,1,3,3-tetramethyldisiloxane (TMDS), and borohydride reagents such as, but not limited to, sodium borohydride and sodium triacetoxyborohydride. Suitable acids for use with the reducing agents may include, but are not limited to, trifluoroacetic acid and methanesulfonic acid. The alcohol of Formula K may then be coupled with the BOC-L-alanine compound of Formula G to produce the compound of Formula L using the reagents and conditions described herein for the preparation of the compound of Formula I in Scheme III. Finally, compound L may be converted into the amine salt compound of Formula C by treatment with strong acid HX described herein. A solution of about three molar equivalents of (4-fluorophenyl)magnesium bromide in THF can be treated at about 0° C. with (S)-ethyl lactate. The diol of Formula H may be recovered by employing standard isolation and purification techniques.

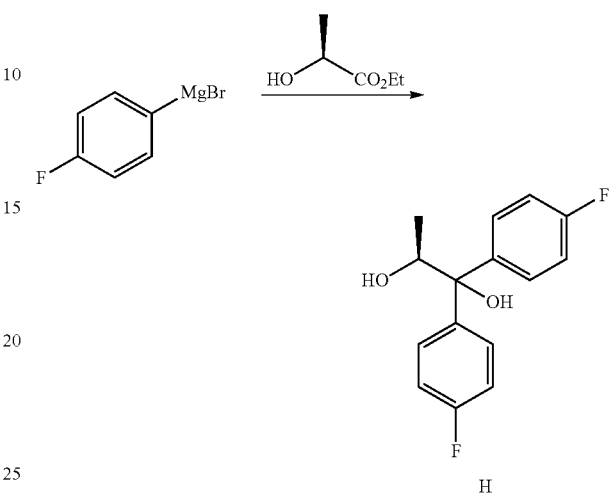

Chemical literature describing the preparation of (S)-(1,1-bis-aryl)propane-1,2-diols like the compound of Formula H include: (1) *Eur. J. Org. Chem.* 2005, 1082, (2) *Tetrahedron Lett.* 1989, 30, 3659, (3) *Tetrahedron: Asymmetry,* 1990, 1, 199, and (4) U.S. Pat. No. 4,628,120. For related transformations involving aryl Grignard addition to (S)-

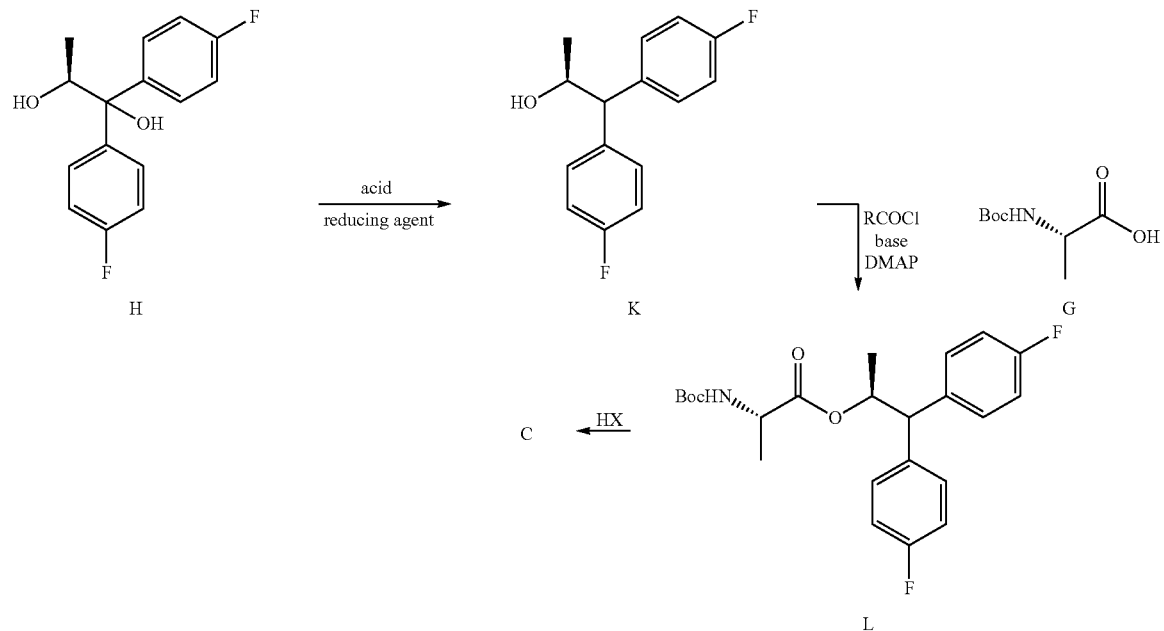

Scheme IV utilizing anhydrous conditions, wherein HX may be selected from HCl, HBr, $H_2SO_4$, $H_3PO_4$ or $CH_3SO_3H$.

C. Preparation of Compound of Formula H

The diol of Formula H may be prepared from (4-fluorophenyl)magnesium bromide and (S)-ethyl lactate as isopropyl lactate, for the synthesis of (S)-(1,1-bisaryl)propane-1,2-diols, see *J. Am. Chem. Soc.* 1990, 112, 3949.

D. Preparation of Compound of Formula B

The conversion of the 4-methoxy-3-hydroxypicolinic acid to the 3-acetoxy compound of Formula B, may be accomplished by acetylating the compound of Formula D with one or more acetylation reagents selected from acetic anhydride and acetyl chloride, bases selected from pyridine, alkyl substituted pyridines, and trialkylamines, or utilization of Schotten-Baumann reaction conditions.

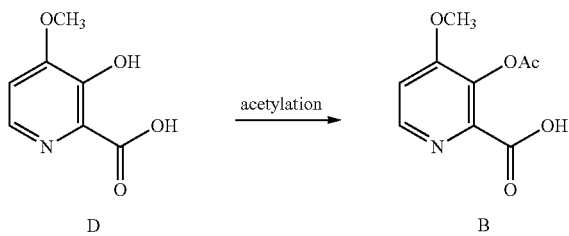

The product obtained by any of these processes, can be recovered by conventional means, such as evaporation, filtration or extraction, and can be purified by standard procedures, such as by recrystallization or chromatography.

The following examples are presented to illustrate the disclosure.

EXAMPLES

Example 1a. (S,S)-1,1-bis(4-fluorophenyl)-propan-2-yl 2-(3-acetoxy-4-methoxypicolinamido)propanoate

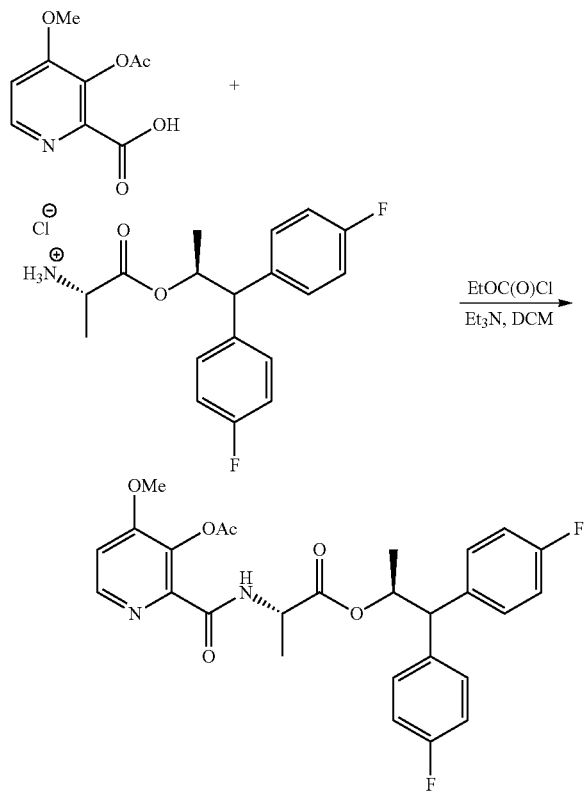

A 100 mL flask equipped with a stir bar was charged with 3-acetoxy-4-methoxypicolinic acid (427 mg, 2 mmol) and DCM (10 mL). The suspension was cooled to −5° C. Triethylamine (445 mg, 4.4 mmol) was added in one portion, followed by addition of ethyl carbonochloridate (0.19 mL, 2 mmol) slowly via syringe. After 10 minutes, a solution of (S,S)-1,1-bis(4-fluorophenyl)propan-2-yl 2-aminopropanoate hydrochloride (712 mg, 2 mmol) in DCM (2 mL) was added. After the reaction appeared complete by HPLC, 20% aqueous $K_2CO_3$ solution (10 mL) was charged, and the mixture was stirred vigorously for 30 min at rt. The organic layer was separated. The aqueous layer was extracted with DCM. The combined organic layers were washed with water, 1N HCl and water. The separated organic layer was concentrated to provide a light yellow foam (1.5 g, 98%): $^1$H NMR (400 MHz, $CDCl_3$) δ 8.39 (s, 1H), 8.32 (d, J=5.4 Hz, 1H), 7.26-7.16 (m, 4H), 7.03-6.87 (m, 5H), 5.71 (dq, J=9.6, 6.1 Hz, 1H), 4.55 (dd, J=8.0, 7.1 Hz, 1H), 4.04 (d, J=9.6 Hz, 1H), 3.91 (s, 3H), 2.38 (s, 3H), 1.22 (d, J=6.1 Hz, 3H), 0.99 (d, J=7.2 Hz, 3H); $^{19}$F NMR (376 MHz, $CDCl_3$) δ −115.61, −115.96; HRMS-ESI (m/z) [M+H]+ calcd for $C_{27}H_{27}F_2N_2O_6$, 512.1759; found, 513.1825.

Example 1b. (S,S)-1,1-bis(4-fluorophenyl)-propan-2-yl 2-(3-acetoxy-4-methoxypicolinamido)propanoate

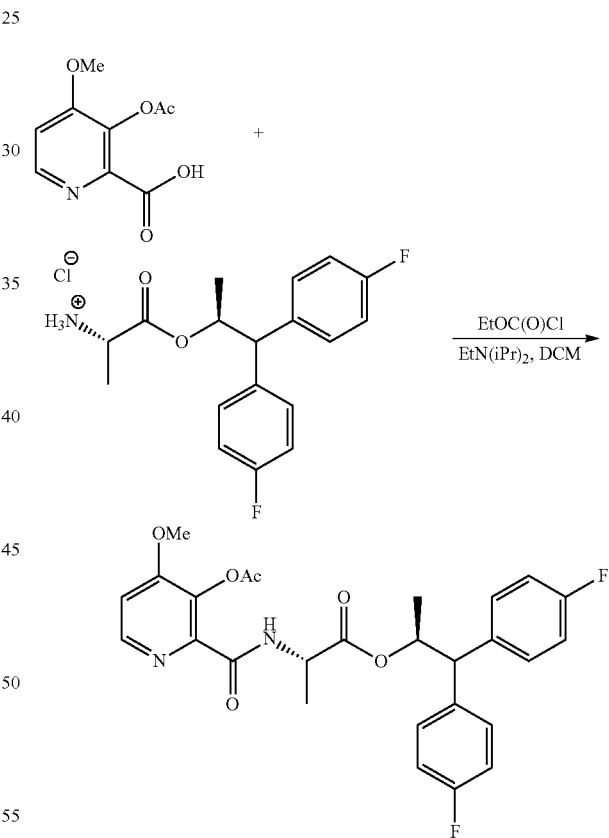

Dichloromethane (64.6 L) and 3-acetoxy-4-methoxypicolinic acid (6.82 kg) were charged to a stainless steel reactor with stirring under nitrogen atmosphere at 25-30° C. The solution was cooled to −15° C., and N,N-diisopropylethylamine (9.2 kg, 2.2 eq) was added dropwise and stirred for 5 min. Ethyl chloroformate (3.68 kg, 1.05 eq) was added dropwise and stirred for 30 min. Finally, a solution of 11.5 kg of (S,S)-1,1-bis(4-fluorophenyl)propan-2-yl 2-aminopropanoate hydrochloride in 32.2 L dichloromethane added dropwise and stirred at −15° C. for 30 min. The reaction mixture was warmed to 0-2° C., and saturated aqueous sodium bicarbonate solution (57.5 L, 5.75 kg of NaHCO₃ in 57.5 L water) was added and stirred for 10-15 min. The aqueous layer was separated and extracted with dichloromethane (1×57.5 L). Combined the organic layers, washed with water (1×57.5 L), then with mixture of 1N HCl and brine solution (1×64.4 L, 32.2 L 1N HCl and 32.2 L brine). Organic layer was dried with sodium sulphate (11.5 kg), filtered, washed with dichloromethane (23.0 L) and concentrated below 40° C. under vacuum (500-600 mm Hg) until no distillate was observed. Added isopropyl alcohol (23.0 L) and concentrated below 45° C. under vacuum (500-600 mm Hg) to give a thick syrup. Isopropyl alcohol (11.5 L) and n-heptane (11.5 L) were charged, heated to 50-55° C. and stirred at 50-55° C. for 30 min. The solution was cooled to 25-30° C., n-heptane (11.5 L) was added, and the solution was stirred at 25-30° C. for 5 h. Additional n-heptane (34.5 L) was added, the solution was stirred at 25-30° C. for 6 h. The resulting solid was filtered, washed with n-heptane (57.5 L) and dried at 35-40° C. under vacuum (500-600 mm Hg) to give (S,S)-1,1-bis(4-fluorophenyl)-propan-2-yl 2-(3-acetoxy-4-methoxypicolinamido)propanoate as an off-white powder (14.74 kg, 89.0% yield). HPLC (Zorbax SB-Phenyl, (250×4.6) mm, 5.0 μm; 0.1% Formic acid in 50:50 water: ACN, Flow rate: 1.0 mL/min) showed the product to be 98.3% pure.

Example 1c. (S,S)-1,1-bis(4-fluorophenyl)-propan-2-yl 2-(3-acetoxy-4-methoxypicolinamido)propanoate

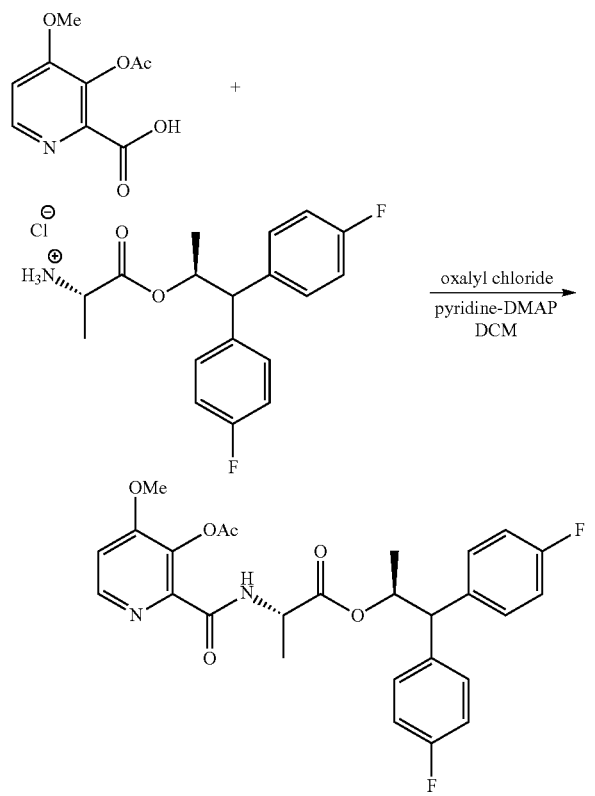

A 500 mL flask equipped with magnetic stir bar and nitrogen inlet was charged with 3-acetoxy-4-methoxypicolinic acid (11.5 g, 54.5 mmol), DCM (140 ml), pyridine (4.84 ml, 59.9 mmol) & 1 drop of DMF. The flask was cooled to 0° C., and oxalyl chloride (4.77 ml, 54.5 mmol) was slowly added via syringe. The resulting dark solution was allowed to stir for approximately 15 min. The solution was then added via cannula to a cold (0° C.) suspension of (S,S)-1,1-bis(4-fluorophenyl)propan-2-yl 2-aminopropanoate hydrochloride (19.38 g, 54.5 mmol) and triethylamine (15.94 ml, 114 mmol) in DCM (70 ml) in a 1 L flask. When the addition was complete, the bath was removed, and the solution was allowed to warm to rt. Upon completion of the reaction as judged by LCMS, the reaction mixture was poured into saturated aqueous NH₄Cl solution (200 mL) and transferred to a separatory funnel. The organic layer was separated, and the aqueous layer was extracted with CH₂Cl₂ (1×200 mL). The combined organic layers were dried with Na₂SO₄, filtered and concentrated to afford a tan foam/black oil. The crude material was purified via silica gel chromatography (0-100% gradient ethyl acetate in hexanes) to afford the title compound as a pink solid foam (14 g, 50.2%, 90% purity): spectroscopic data identical to that listed above.

Example 1d. (S,S)-1,1-bis(4-fluorophenyl)-propan-2-yl 2-(3-acetoxy-4-methoxypicolinamido)propanoate

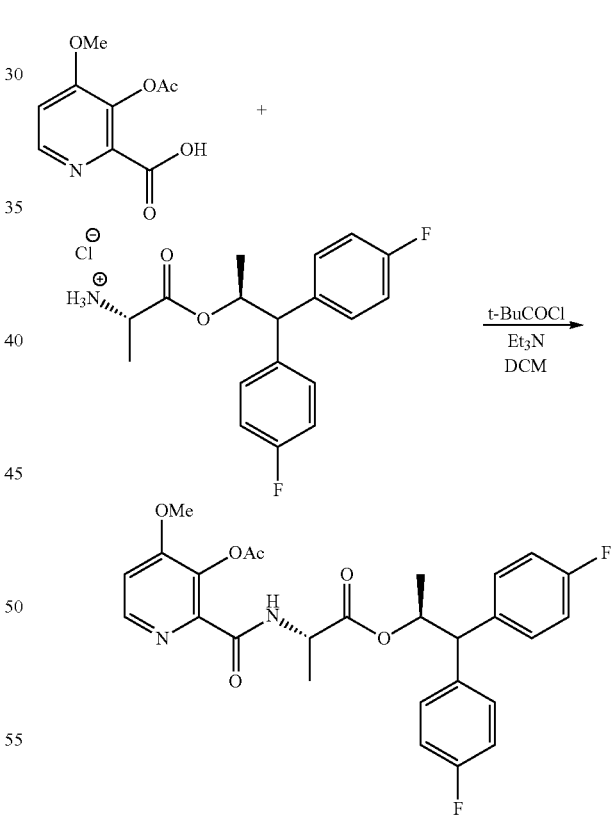

A 100 mL flask equipped with magnetic stir bar and nitrogen inlet was charged with 3-acetoxy-4-methoxypicolinic acid (1.00 g, 4.74 mmol), DCM (23.7 ml), and triethylamine (0.661 ml, 4.74 mmol). The flask was cooled to 0° C., and pivaloyl chloride (0.583 ml, 4.74 mmol) was slowly added to the reaction mixture. The reaction mixture was allowed to stir for 15 min at 0° C. (S,S)-1,1-bis(4-fluorophenyl)propan-2-yl 2-aminopropanoate hydrochloride (1.685 g, 4.74 mmol) was then added in one portion. The reaction mixture was poured into saturated aqueous NH₄Cl solution and transferred to a separatory funnel. The organic layer was separated, washed with saturated aqueous NaHCO₃ solution, then brine and then dried with Na₂SO₄. The solution was filtered and concentrated to afford a an off-white foam. The crude material was purified via silica gel chromatography (0-100% gradient ethyl acetate in hexanes) to afford the title compound as a white foam (1.7 g, 59.5%, 90% purity): spectroscopic data identical to that listed above.

Example 1e. (S,S)-1,1-bis(4-fluorophenyl)-propan-2-yl 2-(3-((ethoxycarbonyl)oxy)-4-methoxypicolinamido)propanoate

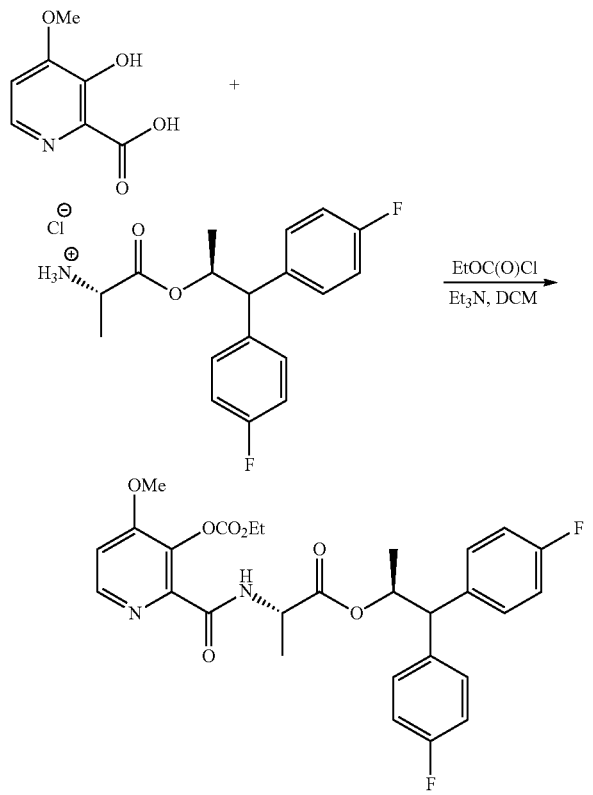

A 250 mL flask equipped with a stir bar was charged with 3-hydroxy-4-methoxypicolinic acid (0.846 g, 5 mmol) and backfilled with nitrogen. DCM (25 mL) was added to the reaction flask and the resulting white heterogeneous mixture was cooled to 0° C. Triethylamine (2.3 mL, 16.5 mmol) was added and the reaction mixture became a homogeneous colorless solution over the course of ten minutes of vigorous stirring. Ethyl chloroformate (1.0 mL, 10.5 mmol) was slowly added to the reaction mixture and a white precipitate began to form. After stirring for 15 min at 0° C., (S,S)-1,1-bis(4-fluorophenyl)propan-2-yl 2-aminopropanoate hydrochloride (1.78 g, 5.00 mmol) was added to the flask in one portion. The reaction mixture was stirred at 0° C. for 3 min, at which time the reaction was quenched with 20 mL of water and 5 mL of 2N HCl. The biphasic mixture was diluted with DCM and transferred to a separatory funnel. The layers were separated and the organic layer was dried with Na₂SO₄, filtered and concentrated to afford a pale yellow oil. The crude material was purified via silica gel chromatography by eluting with an ethyl acetate/hexane gradient to afford the title compound as a white solid (2.3 g, 85%): mp 48-64° C.; $^1$H NMR (400 MHz, CDCl₃) δ 8.45-8.25 (m, 2H), 7.38-7.12 (m, 4H), 7.09-6.85 (m, 5H), 5.71 (dq, J=9.7, 6.2 Hz, 1H), 4.67-4.54 (m, 1H), 4.34 (q, J=7.1 Hz, 2H), 4.04 (d, J=9.6 Hz, 1H), 3.92 (s, 3H), 1.40 (t, J=7.1 Hz, 3H), 1.22 (d, J=6.2 Hz, 3H), 0.99 (d, J=7.2 Hz, 3H); $^{13}$C NMR (101 MHz, CDCl₃) δ 172.1, 162.2, 161.7 (d, J=246.0 Hz), 161.6 (d, J=245.6 Hz), 159.4, 152.5, 146.8, 141.7, 137.7, 136.9, 136.8, 129.6 (d, J=7.8 Hz), 129.5 (d, J=7.8 Hz), 115.7 (d, J=21.4 Hz), 115.4 (d, J=21.2 Hz), 110.0, 73.1, 65.4, 56.3, 56.1, 47.8, 19.1, 18.1, 14.1; $^{19}$F NMR (471 MHz, CDCl3) δ −115.59, −115.95; HRMS-ESI (m/z) [M+H]+ calcd for C₂₈H₂₉F₂N₂O₇, 543.1937; found, 543.1932.

Example 1f. (S,S)-1,1-bis(4-fluorophenyl)-propan-2-yl 2-(3-((isobutoxycarbonyl)oxy)-4-methoxypicolinamido)propanoate

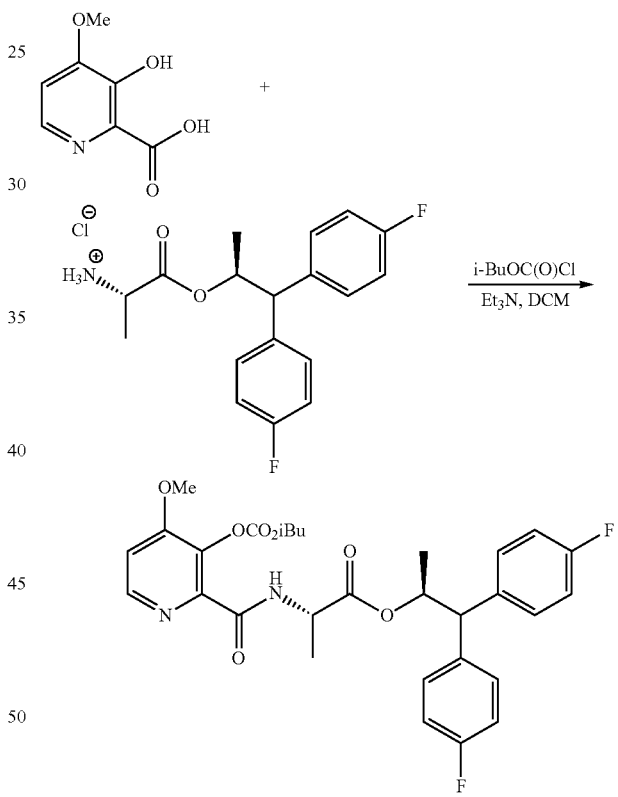

A 250 mL flask equipped with a stir bar was charged with 3-hydroxy-4-methoxypicolinic acid (0.846 g, 5 mmol) and backfilled with nitrogen. DCM (25 mL) was added to the reaction flask and the resulting white heterogeneous mixture was cooled to 0° C. Triethylamine (2.3 mL, 16.5 mmol) was added and the reaction mixture became a homogeneous colorless solution over the course of ten minutes of vigorous stirring. Isobutyl chloroformate (1.4 mL, 10.5 mmol) was slowly added to the reaction mixture and a white precipitate began to form. After stirring for 15 min at 0° C., (S,S)-1,1-bis(4-fluorophenyl)propan-2-yl 2-aminopropanoate hydrochloride (1.78 g, 5.00 mmol) was added to the flask in one portion. The reaction mixture was stirred at 0° C. for 3 min, at which time the reaction was quenched with 20 mL of water and 5 mL of 2N HCl. The biphasic mixture was diluted with DCM and transferred to a separatory funnel. The layers were separated and the organic layer was dried with Na$_2$SO$_4$, filtered and concentrated to afford a pale yellow oil. The crude material was purified via silica gel chromatography by eluting with an ethyl acetate/hexane gradient to afford the title compound as a white solid (2.3 g, 81%): mp 47-63° C.; $^1$H NMR (400 MHz, CDCl$_3$) δ 8.38-8.26 (m, 2H), 7.26-7.18 (m, 4H), 7.04-6.88 (m, 5H), 5.71 (dq, J=9.6, 6.2 Hz, 1H), 4.66-4.51 (m, 1H), 4.07 (d, J=6.7 Hz, 2H), 4.04 (d, J=10.0 Hz, 1H), 3.92 (s, 3H), 2.19-1.98 (m, 1H), 1.22 (d, J=6.1 Hz, 3H), 0.99 (d, J=6.7 Hz, 6H), 0.99 (d, J=7.2 Hz, 3H); $^{13}$C NMR (101 MHz, CDCl$_3$) δ 172.2, 162.2, 161.73 (d, J=246.0 Hz), 161.65 (d, J=245.6 Hz), 159.4, 152.6, 146.8, 141.7, 137.8, 136.9, 136.9, 129.61 (d, J=7.8 Hz), 129.54 (d, J=8.0 Hz), 115.68 (d, J=21.3 Hz), 115.39 (d, J=21.3 Hz), 109.9, 75.3, 73.1, 56.3, 56.1, 47.8, 27.8, 19.1, 18.9, 18.1; $^{19}$F NMR (471 MHz, CDCl$_3$) δ −115.59, −115.95; HRMS-ESI (m/z) [M+H]+ calcd for C$_{30}$H$_{33}$F$_2$N$_2$O$_7$, 571.2250; found, 571.2253.

Example 1g. (S,S)-1,1-bis(4-fluorophenyl)-propan-2-yl 2-(3-hydroxy-4-methoxypicolinamido)propanoate stir for 3 h at RT. The reaction was acidified to pH of 2 with 2N HCl (0.8 mL) and diluted with 25 mL of ethyl acetate. The organic layer was concentrated to give a yellow oil. The crude material was purified via silica gel chromatography by eluting with an ethyl acetate/hexane gradient to afford the title compound as a white foam (397 mg, 84%): $^1$H NMR (400 MHz, CDCl$_3$) δ 12.06 (s, 1H), 8.32 (dd, J=6.7, 4.3 Hz, 1H), 7.98 (d, J=5.2 Hz, 1H), 7.32-7.14 (m, 4H), 7.03-6.89 (m, 4H), 6.87 (d, J=5.2 Hz, 1H), 5.73 (dq, J=9.8, 6.2 Hz, 1H), 4.61-4.47 (m, 1H), 4.05 (d, J=9.8 Hz, 1H), 3.94 (s, 3H), 1.25 (d, J=6.1 Hz, 3H), 1.07 (d, J=7.2 Hz, 3H); 13C NMR (101 MHz, CDCl3) δ 171.6, 168.6, 161.8 (d, J=246.1 Hz), 161.7 (d, J=245.7 Hz), 155.4, 148.8, 140.4, 136.8 (d, J=3.4 Hz), 136.7 (d, J=3.4 Hz), 130.4, 129.5 (d, J=7.8 Hz), 129.5 (d, J=7.8 Hz), 115.7 (d, J=21.3 Hz), 115.4 (d, J=21.3 Hz), 109.5, 73.3, 56.1, 56.1, 47.9, 19.1, 17.7; $^{19}$F NMR (471 MHz, CDCl$_3$) δ −115.46, −115.80; HRMS-ESI (m/z) [M+H]+ calcd for C$_{25}$H25F2N2O5, 471.1726; found, 471.1724.

Example 1h. (S,S)-1,1-bis(4-fluorophenyl)-propan-2-yl 2-(3-acetoxy-4-methoxypicolinamido)propanoate

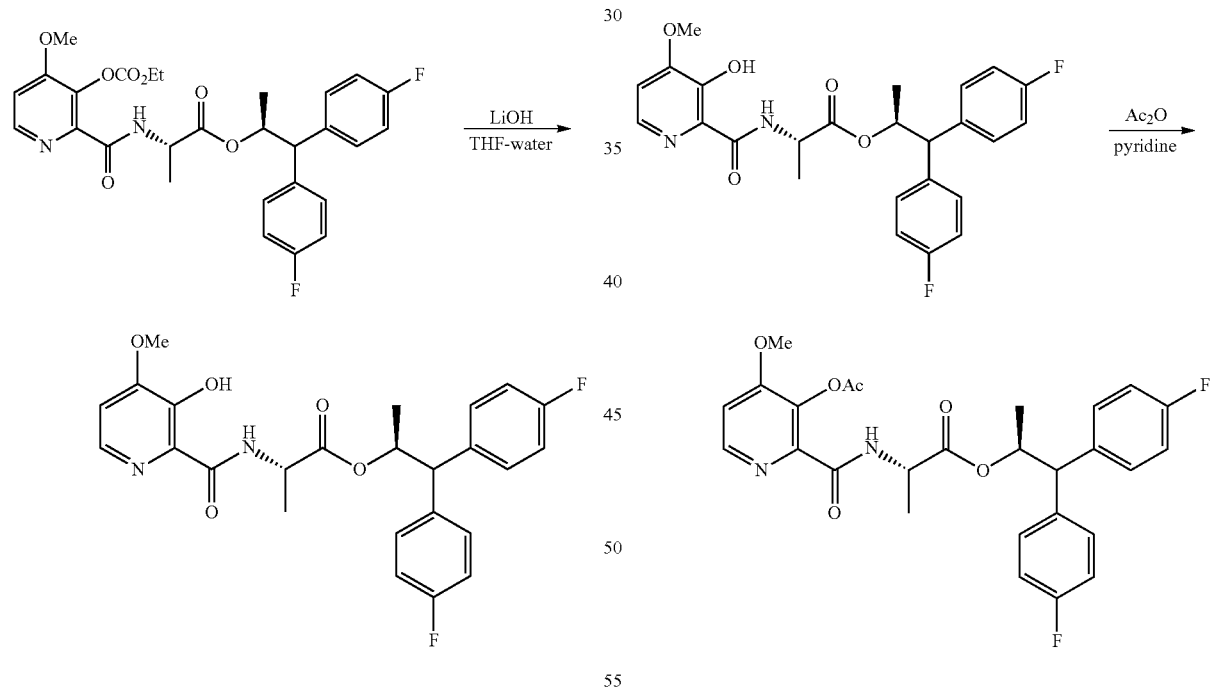

A vial equipped with a stir bar was charged with (S,S)-1,1-bis(4-fluorophenyl)propan-2-yl 2-(3-((ethoxycarbonyl)oxy)-4-methoxypicolinamido)propanoate (543 mg, 1 mmol, employed as an 8:1 mixture of the title starting material to product: (S,S)-1,1-bis(4-fluorophenyl)propan-2-yl 2-(3-hydroxy-4-methoxypicolinamido)propanoate) and THF (5 mL). Lithium hydroxide hydrate (71 mg, 1.69 mmol) was placed in a separate vial, dissolved in water (2.5 mL) and added to the reaction flask. The reaction immediately turned from clear colorless to yellow. The reaction was allowed to A 2 L flask equipped with a stir bar was charged with (S,S)-1,1-bis(4-fluorophenyl)-propan-2-yl 2-(3-hydroxy-4-methoxypicolinamido)propanoate (25 g, 51.0 mmol), pyridine (250 mL) and acetic anhydride (250 mL, 2.65 mol). The reaction was stirred for 1 h at RT and then the solvents were removed under vacuum. Heptane was added and the mixture was concentrated. This step was repeated to ensure complete azeotropic removal of any residual solvent. Dichloromethane and sat. aqueous ammonium chloride were added to the residue and the layers were separated. The aqueous layer was extracted with dichloromethane (1×) and the combined organic layers were dried over Na$_2$SO$_4$, filtered and concentrated under vacuum to yield an off-white foam. The crude material was purified via silica gel chromatography by eluting with an ethyl acetate/hexane gradient to afford the title compound as a white foam (25.1 g, 95%, 99% purity): $^1$H NMR (500 MHz, CDCl$_3$) δ 8.39 (s, br, 1H), 8.32 (d, J=5.4 Hz, 1H), 7.26-7.19 (m, 4H), 7.04-6.88 (m, 5H), 5.71 (dq, J=9.6, 6.1 Hz, 1H), 4.62-4.49 (m, 1H), 4.04 (d, J=9.6 Hz, 1H), 3.90 (s, 3H), 2.38 (s, 3H), 1.22 (d, J=6.2 Hz, 3H), 0.99 (d, J=7.1 Hz, 3H); 13C NMR (126 MHz, CDCl3) δ 172.2, 170.3, 162.9, 161.7 (d, J=246.1 Hz), 161.6 (d, J=245.6 Hz), 160.3, 145.7, 144.0, 142.4, 136.9 (d, J=3.3 Hz), 136.8 (d, J=3.4 Hz), 129.6 (d, J=5.9 Hz), 129.5 (d, J=5.8 Hz), 115.7 (d, J=21.3 Hz), 115.4 (d, J=21.1 Hz), 109.6, 73.0, 56.2, 56.1, 48.0, 20.9, 19.2, 17.8; $^{19}$F NMR (471 MHz, CDCl$_3$) δ -115.60, -115.96; HRMS-ESI (m/z) [M+H]+ calcd for C$_{27}$H27F2N2O6, 513.1832; found, 513.1849.

Example 1i. (S,S)-1,1-bis(4-fluorophenyl)-propan-2-yl 2-(3-acetoxymethoxy-4-methoxypicolinamido)propanoate

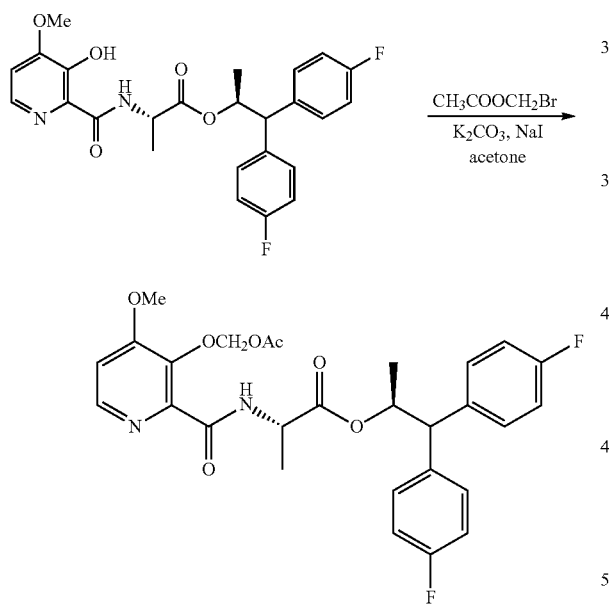

A three-neck 500 mL flask equipped with a stirbar, reflux condenser, thermocouple and nitrogen inlet was charged with (S,S)-1,1-bis(4-fluorophenyl)-propan-2-yl 2-(3-hydroxy-4-methoxypicolinamido)propanoate (4.9 g, 10.42 mmol)) and acetone (104 ml). Solid potassium carbonate (2.88 g, 20.83 mmol) was added, followed by the addition of bromomethyl acetate (1.532 ml, 15.62 mmol). A catalytic amount of NaI was added, and the mixture was heated to 50° C. for three hours. The mixture was cooled, filtered and concentrated. The crude material was purified via silica gel chromatography by eluting with an ethyl acetate/hexane gradient to afford the title compound as a white foam (3.9 g, 69%): $^1$H NMR (400 MHz, CDCl$_3$) δ 8.26 (d, J=5.4 Hz, 1H), 8.20 (d, J=7.8 Hz, 1H), 7.28-7.18 (m, 4H), 7.02-6.91 (m, 5H), 5.76-5.70 (m, 1H), 5.72 (s, 2H), 4.56 (9, J=7.3 Hz, 1H), 4.05 (d, J=9.7 Hz, 1H), 3.91 (s, 3H), 2.06 (s, 3H), 1.24 (d, J=6.1 Hz, 3H), 1.00 (d, J=7.2 Hz, 3H); $^{13}$C NMR (101 MHz, CDCl$_3$) δ 172.2, 170.3, 162.9, 161.7 (d, J=246.0 Hz), 161.6 (d, J=245.5 Hz), 160.3, 145.7, 144.0, 142.3, 136.9 (d, J=3.3 Hz), 136.8 (d, J=3.3 Hz), 129.6 (d, J=7.8 Hz), 129.5 (d, J=7.9 Hz), 115.7 (d, J=21.4 Hz), 115.4 (d, J=21.3 Hz), 109.6, 89.5, 73.0, 56.2, 56.1, 48.1, 20.8, 19.1, 17.8; $^{19}$F NMR (376 MHz, CDCl$_3$) δ -115.59, -115.97; HRMS-ESI (m/z) [M+H]$^+$ calcd for C$_{28}$H$_{29}$F$_2$N$_2$O$_7$, 543.1937; found, 543.1948.

Example 1j. (S,S)-1,1-bis(4-fluorophenyl)-1-hydroxypropan-2-yl 2-((tert-butoxycarbonyl)amino)propanoate

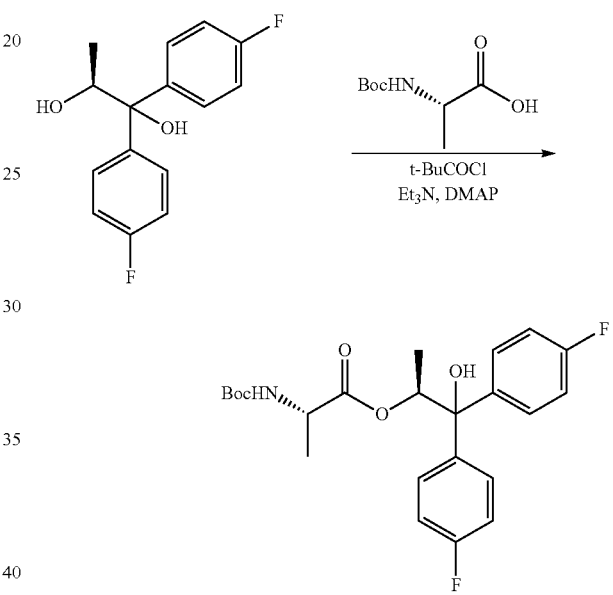

A 250 mL flask equipped with a stir bar was charged with (S)-2-[(tert-butoxycarbonyl)amino]propanoic acid (5.68 g, 30.0 mmol) and DCM (125 ml) and cooled to 0° C. Triethylamine (8.72 mL, 62.5 mmol) was added to the reaction flask. As pivaloyl chloride (3.69 ml, 30.0 mmol) was slowly added to the reaction mixture a white precipitate began to form. After stirring for 15 min at 0° C., (S)-1,1-bis(4-fluorophenyl)propane-1,2-diol (6.61 g, 25 mmol) was added, followed by N,N-dimethylpyridin-4-amine (0.153 g, 1.250 mmol) which led to an exotherm up to 4.4° C. After the additions, the reaction was stirred for 2 h at RT. The reaction was quenched with water, and the layers were separated. The aqueous layer was extracted once with DCM. The combined organic layers were dried with Na$_2$SO$_4$, filtered and concentrated to afford an oil. The crude material was purified via silica gel chromatography by eluting with an ethyl acetate/hexane gradient to afford the title compound as a white solid (8.75 g, 80%): mp 50-60° C.; $^1$H NMR (400 MHz, CDCl$_3$) δ 7.50-7.42 (m, 2H), 7.42-7.36 (m, 2H), 7.03-6.94 (m, 4H), 5.91 (q, J=6.2 Hz, 1H), 4.96 (d, J=7.8 Hz, 1H), 4.20-4.10 (m, 1H), 3.02-2.73 (m, 1H), 1.41 (s, 8H), 1.18 (d, J=6.3 Hz, 3H), 0.92 (d, J=7.2 Hz, 3H); $^{13}$C NMR (101 MHz, CDCl$_3$) δ 172.4, 161.9 (d, J=246.7 Hz), 161.9 (d, J=246.7 Hz), 155.0, 140.7 (d, J=3.3 Hz), 138.6 (d, J=2.8 Hz), 127.5 (d, J=8.0 Hz), 127.4 (d, J=8.2 Hz), 115.2 (d, J=21.6 Hz), 80.0, 79.0, 74.9, 49.2, 28.3, 18.0, 14.4 (one peak is missing due to incidental equivalence); $^{19}$F NMR (376 MHz, CDCl$_3$) δ −115.21, −115.25; HRMS-ESI (m/z) [M+Na]+ calcd for C$_{23}$H27F2NNaO5, 458.1750; found, 458.1760.

Example 1k. (S,S)-1,1-bis(4-fluorophenyl)-1-hydroxypropan-2-yl 2-((tert-butoxycarbonyl)amino)propanoate

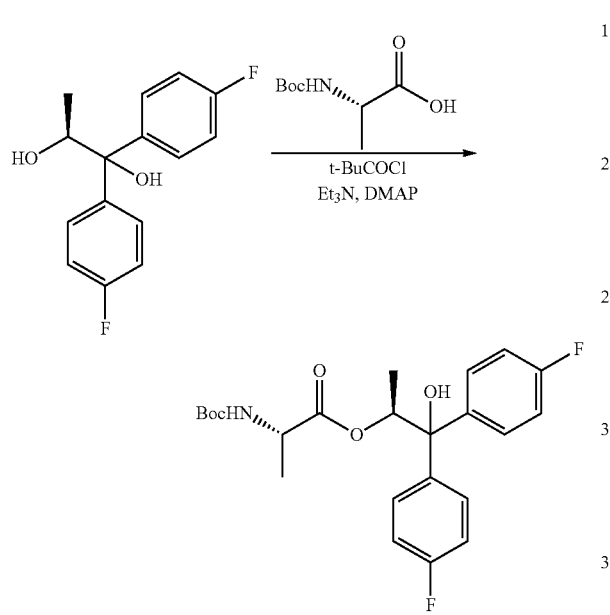

Anhydrous THF (49.4 L, 7.6 volume) and Boc-L-alanine (6.3 kg, 1.35 eq) were charged into a stainless steel reactor with stirring under nitrogen atmosphere at 25-30° C. The reaction mixture was cooled to 0-3° C., and triethylamine (9.7 L, 2.8 eq) was added dropwise at 0-3° C. and stirred for 5 min. Pivaloyl chloride (4.0 Kg, 1.35 eq) was added dropwise at 0-3° C. and stirred at 0-3° C. for 1 h. 4-(Dimethylamino)pyridine (0.15 kg, 0.05 eq) was added in one portion and stirred for 5 min. Finally, a solution of (S)-1,1-bis(4-fluorophenyl)propane-1,2-diol in THF (6.5 kg, 1.0 eq in 19.5 L of THF) was added dropwise at 0-3° C. The reaction mixture was stirred at 25-30° C. for 3 h. The reaction mixture was concentrated below 40° C. under vacuum (500-600 mm Hg) until no distillate was observed. Ethyl acetate (49.4 L) and water (24.7 L) were added and stirred for 10 min. The layers were separated. The organic layer was washed with saturated ammonium chloride solution (1×24.7 L), then with saturated sodium bicarbonate solution (1×24.7 L) and brine solution (1×13.0 L,). The organic layer was dried with sodium sulphate (3.25 kg), filtered, washed with ethyl acetate (6.5 L) and concentrated completely below 40° C. under vacuum (500-600 mm Hg) until no distillate was observed. Added hexanes (10.4 L) and concentrated below 40° C. under vacuum (500-600 mm Hg) to give a thick syrup. Hexanes (13.0 L) were added and stirred at 25-30° C. for 10 min. The solution was seeded with authentic product (13.0 g) and stirred at 25-30° C. for 12 h. The solid was filtered, washed with hexanes (2×6.5 L, 2.0 volume) and dried at 38-42° C. under vacuum (500-600 mm Hg) to give (S,S)-1,1-bis(4-fluorophenyl)-1-hydroxypropan-2-yl 2-((tert-butoxycarbonyl)amino)propanoate as off white solid (8.4 kg, 78.4% yield). HPLC (Hypersil BDS C18, (250×4.6) mm, 5.0 µm; A: 0.1% TFA in water, B: ACN, Flow: 1.0 mL/min) showed the product to be 94.0% pure.

Example 11.
(S,S)-1,1-bis(4-fluorophenyl)propan-2-yl 2-aminopropanoate Hydrochloride

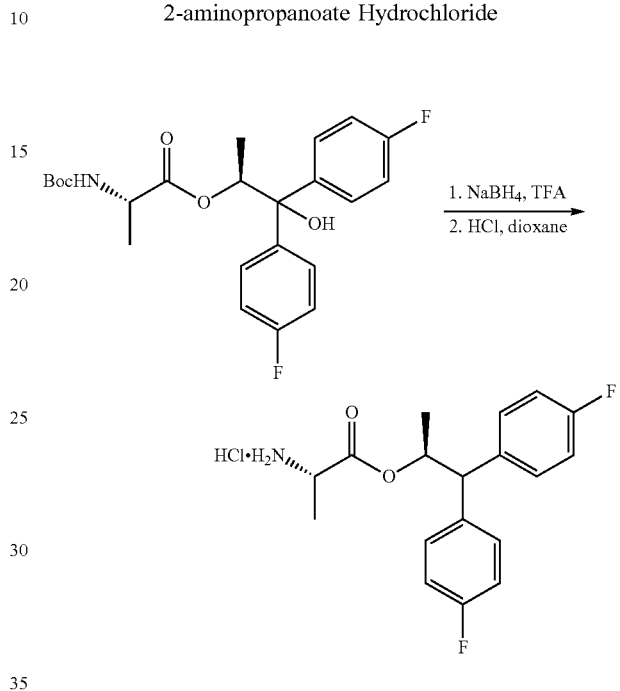

A 3 neck flask equipped with a stir bar, temperature probe and nitrogen inlet was charged with trifluoroacetic acid (8.85 ml, 115 mmol) and cooled to 0° C. Sodium borohydride (0.434 g, 11.5 mmol) was slowly added, followed by slow addition of (S,S)-1,1-bis(4-fluorophenyl)-1-hydroxypropan-2-yl 2-((tert-butoxycarbonyl)amino)propanoate (1 g, 2.3 mmol) in DCM (2.3 mL). The reaction mixture was stirred at 0° C. for 1 h and then at RT for 3 h. The reaction mixture was quenched with 2M NaOH to pH >12, and diluted with DCM. The organic layer was washed with brine. The combined aqueous layers were extracted once with DCM. The combined organic layers were concentrated to give an oil. The crude free base of the amine was treated with 2 mL of 4M HCl in dioxane and then concentrated to give a pink gummy oil. MTBE (2 mL) was added and a white precipitate began to form. The heterogeneous mixture was stirred for 30 min at 0° C. Vacuum filtration of the heterogeneous mixture afforded the title compound as a white solid (355 mg, 40%): $^1$H NMR (300 MHz, DMSO-d6) δ 8.38 (s, 3H), 7.56-7.40 (m, 4H), 7.18-7.10 (m, 4H), 5.77 (dq, J=12.2, 6.2 Hz, 1H), 4.27 (d, J=10.1 Hz, 1H), 3.91 (q, J=7.1 Hz, 1H), 1.17 (d, J=6.1 Hz, 3H), 0.81 (d, J=7.2 Hz, 3H); $^{13}$C NMR (101 MHz, DMSO-d6) δ 169.5, 161.0 (d, J=243.2 Hz), 160.9 (d, J=242.7 Hz), 137.8 (d, J=3.2 Hz), 137.3 (d, J=3.2 Hz), 130.0 (d, J=7.9 Hz), 129.8 (d, J=7.9 Hz), 115.4 (d, J=21.1 Hz), 115.2 (d, J=21.0 Hz), 73.7, 54.7, 47.6, 18.8, 15.0; $^{19}$F NMR (376 MHz, DMSO-d6) δ −115.89, −116.29; ESIMS m/z 320.1 ([M+H]+).

Example 1m.
(S,S)-1,1-bis(4-fluorophenyl)propan-2-yl 2-aminopropanoate Hydrochloride

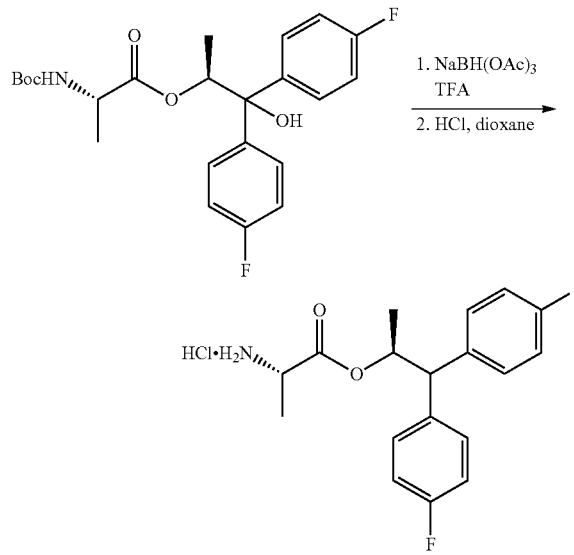

A 3 neck flask equipped with a stir bar, temperature probe and nitrogen inlet was charged with sodium triacetoxyborohydride (4.24 g, 20 mmol) and trifluoroacetic acid (15.4 ml, 200 mmol) at 0° C. After 10-15 minutes at 0-5° C., (S,S)-1,1-bis(4-fluorophenyl)-1-hydroxypropan-2-yl 2-((tert-butoxycarbonyl)amino)propanoate (4.35 g, 10 mmol) in DCM (5 mL) was added. The reaction mixture was stirred at rt for 4-5 h. The reaction mixture was concentrated and rediluted with DCM. The organic layer was washed with aqueous 20% K₂CO₃ solution. The aqueous layer was extracted with additional DCM. The combined organic layers were washed with water. The organic layer was concentrated to give an oil. The crude free base of the amine was diluted with MTBE then treated with 4M HCl in dioxane (3.0 mL). The white precipitate began to form. The heterogeneous mixture was stirred for 0.5-1 hour at RT. Vacuum filtration of the solid product afforded the title compound as a white solid (2.7 g, 75%): spectroscopic data were identical to the compound isolated in Example 11.

Example 1n.
(S,S)-1,1-bis(4-fluorophenyl)propan-2-yl 2-aminopropanoate Hydrochloride

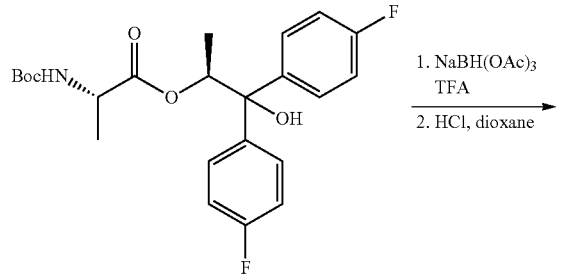

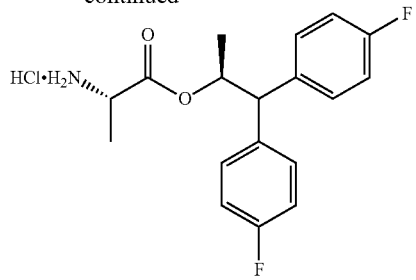

Trifluoroacetic acid (170.3 L) was charged in to a glass-lined reactor with stirring under nitrogen atmosphere at 25-30° C. and cooled to 0-2° C. Sodium triacetoxyborohydride (29.7 kg, 2.7 eq) was added in portions (4 lots in every 5 min interval) at 0-10° C. and stirred at 13-17° C. for 30 min. A solution of (S,S)-1,1-bis(4-fluorophenyl)-1-hydroxypropan-2-yl-2-((tert-butoxycarbonyl)amino) propanoate in dichloromethane (22.7 kg, 1.0 equiv., in 22.7 L of dichloromethane) was added dropwise by maintaining the temperature at 8-10° C. and stirred at 13-17° C. for 2 h. After completion of the reaction, the reaction mixture was concentrated below 50° C. under vacuum (500-600 mm Hg), then the mass was co-evaporated with toluene (2×90.8 L) to give a pale yellow syrup which was dissolved in dichloromethane (227 L). 15% Aqueous ammonium chloride solution (794.5 L) was added slowly to the above mass at 25-30° C. and stirred at 25-30° C. for 15 min. The layers were separated. The aqueous layer was extracted with dichloromethane (2×113.5 L) The combined organic extracts were washed with brine (1×113.5 L), dried with sodium sulphate (22.7 kg) and filtered. The filtrate was concentrated below 35° C. under vacuum (500-600 mm Hg) to give a pale brown syrup. MTBE (68.1 L) and n-heptane (22.7 L) were added to the syrup and cooled to 8-12° C. 4N HCl in dioxane (20.45 L) was added at 8-12° C. and stirred for 30 min at 25-30° C. Added n-heptane (113.5 L) and stirred at 25-30° C. for 30 min. The resulting solid was filtered under nitrogen and washed with n-heptane (68.1 L) to give a first crop.

The filtrate was concentrated below 50° C. under vacuum (500-600 mm Hg). MTBE (45.4 L) and 4N HCl in dioxane (11.4 L) were added and stirred at 25-30° C. for 1 h. The solution was concentrated below 50° C. under vacuum (500-600 mm Hg) to give a brown syrup. Charged MTBE (22.7 L) and n-heptane (68.1 L), stirred at 25–30° C. for 5 h, filtered under nitrogen and washed with n-heptane (45.4 L, 2.0 volume) to give a second crop.

The two crops, 2-propanol (74.9 L) and n-heptane (74.9 L) were added to a glass-lined reactor and stirred under nitrogen atmosphere at 25-30° C. The above mass was heated to 75-80° C. and maintained at 75-80° C. for 30 min. The mass was slowly cooled to 25-30° C. and maintained at 25-30° C. for 12 h. The solid was filtered, washed with 50% 2-propanol in n-heptane (68.1 L) and dried at 40-45° C. under vacuum (500-600 mm Hg) to give pure (S,S)-1,1-bis(4-fluorophenyl)propan-2-yl 2-aminopropanoate hydrochloride as off white powder (11.54 kg, 62.2% yield). HPLC (Zorbax 300 SCX, (250×4.6) mm, 5.0 μm; 55:45 [200 mm Phosphate buffer (pH: 3):ACN], Flow: 2.0 mL/min) showed the product to be 94.0% pure.

Example 1o.
(S,S)-1,1-bis(4-fluorophenyl)propan-2-yl 2-aminopropanoate Hydrochloride

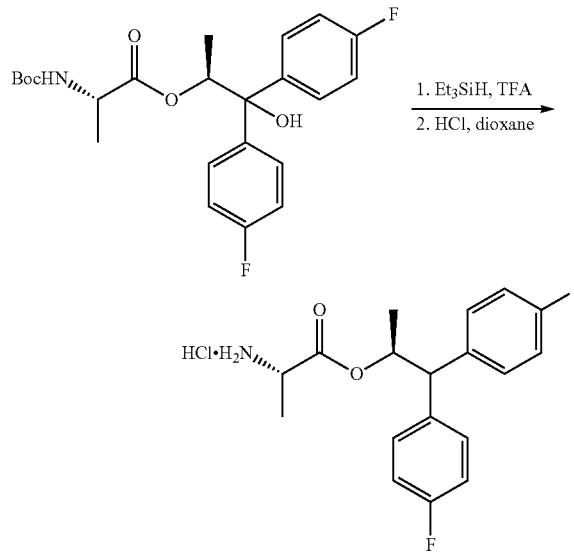

A 25 mL flask equipped with a stir bar, temperature probe and nitrogen inlet was charged with (S,S)-1,1-bis(4-fluorophenyl)-1-hydroxypropan-2-yl 2-((tert-butoxycarbonyl)amino)propanoate (3.0 g, 6.89 mmol) followed by CH$_2$Cl$_2$ (10 mL), and triethylsilane (4.4 mL, 27.56 mmol, 4 eq.). The internal temperature of the flask was maintained at 4° C. with an ice-bath. Trifluoroacetic acid (10 mL, 130 mmol, 19 eq.) was added over 15 minutes. The internal temperature did not exceed 8° C. during the addition. The reaction was warmed to room temperature and stirred for 4 hours. LC-MS indicated complete conversion to product. The solvent was removed under reduced pressure and co-evaporated with CH$_2$Cl$_2$ (3×20 mL). The resulting oil was dissolved in CH$_2$Cl$_2$ (50 mL), and added to a saturated solution of NaHCO$_3$ (100 mL) in small portions over 10 minutes. The aqueous layer was extracted with CH$_2$Cl$_2$ (25 mL), the combined organic layers were washed with brine and dried over Na$_2$SO$_4$ and concentrated under reduced pressure. The oil was dissolved in MTBE (15 mL), and 4N HCl in dioxane was added (1.8 mL) to give a white precipitate. The solid was recrystallized from 2-propanol/heptane, collected by filtration, washed with heptane and dried in a vacuum oven at 50° C. to give 1.85 g of the final compound in 75% yield. Spectroscopic data were identical to the compound isolated in Example 1h.

Example 1p.
(S,S)-1,1-bis(4-fluorophenyl)propan-2-yl 2-aminopropanoate Hydrochloride

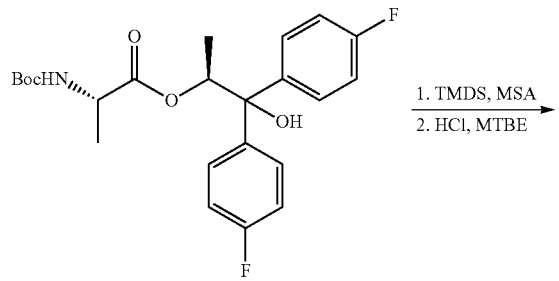

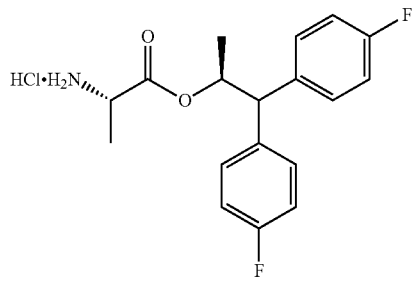

In a 250 mL, three-neck round bottom flask, equipped with a magnetic stir bar, a thermocouple and a nitrogen inlet, a mixture of MsOH (15.0 mL, 230.0 mmol) and CH$_2$Cl$_2$ (15 mL) was cooled to 1° C. 1,1,3,3-tetramethyldisiloxane (TMDS) (4.1 mL, 23.0 mmol) was added. A solution of (S,S)-1,1-bis(4-fluorophenyl)-1-hydroxypropan-2-yl 2-((tert-butoxycarbonyl)amino)propanoate (10.1 g, 23.0 mmol) in CH$_2$Cl$_2$ (15 mL) was added slowly dropwise over the course of an hour to maintain an internal temperature below 3° C. After the addition was complete, the reaction mixture was stirred 45 min at which point the reaction was complete by HPLC analysis. An aqueous solution of sodium carbonate (saturated, 200 mL) was added slowly maintaining an internal temperature below 20° C. The mixture was transferred to a separatory funnel. The layers were separated. The aqueous layer was extracted with CH$_2$Cl$_2$ (20 mL×1). The combined organic layers were cloudy and washed with brine (20 mL×1), dried over sodium sulfate and filtered to give an off-white goo. The crude material was taken up in MTBE (125 mL), and HCl (3 M in CPME, 11.5 mL) was added with stirring. The white solids were collected and washed with heptane (50 mL). The material was allowed to dry overnight in the fume hood. 8.03 g solids were collected (98% yield, 89% purity by HPLC with internal standard). $^1$H NMR (400 MHz, CDCl$_3$) δ 8.64 (bs, 3H), 7.21 (tdd, J=7.2, 5.1, 2.0 Hz, 4H), 6.98 (td, J=8.6, 6.2 Hz, 4H), 5.77-5.59 (m, 1H), 4.05 (d, J=10.0 Hz, 1H), 3.96 (q, J=7.2 Hz, 1H), 1.23 (d, J=6.1 Hz, 3H), 1.14 (d, J=7.2 Hz, 3H). $^{19}$F NMR (376 MHz, CDCl$_3$) δ −115.16, −115.52. ESIMS m/z 320.1 ([M+H]$^+$).

Example 1q. (S)-1,1-bis(4-fluorophenyl)propan-2-ol

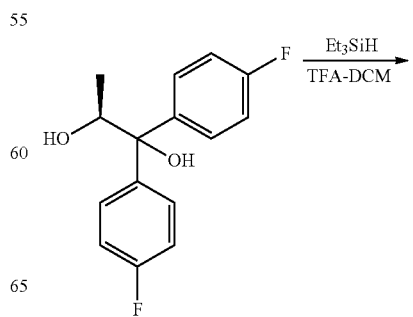

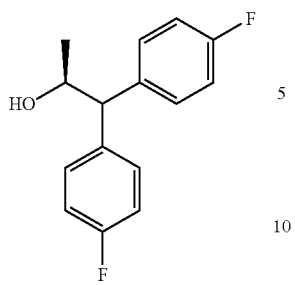

A 5 L flask was charged with (S)-1,1-bis(4-fluorophenyl)propane-1,2-diol (120 g, 431 mmol) and DCM (1200 mL). The flask was cooled to 0° C., and triethylsilane (689 mL, 4314 mmol) was added followed by addition of TFA (332 mL, 4314 mmol). Addition took 12 minutes, and the temperature rose from −3° C. to −2° C. The mixture was stirred at 0° C. for 1 hour. After 1 hr, the reaction mixture was neutralized with 4N NaOH (~1.2 L), while still in the ice bath, to a pH of ~10. The layers were separated and the aqueous phase was extracted with dichloromethane (1×). The combined organic extracts were dried over Na2SO4, filtered and concentrated in vacuo to yield 159 g of a pale-yellow oil. The crude material was loaded onto a 1.5 kg ISCO silica column and eluted with an EtOAc/hexane gradient to afford 90.3 g of a white solid (83%). $^1$H NMR (400 MHz, Chloroform-d) δ 7.35-7.28 (m, 2H), 7.25-7.18 (m, 2H), 7.05-6.93 (m, 4H), 4.45 (m, 1H), 3.79 (d, J=8.3 Hz, 1H), 1.63 (d, J=3.7 Hz, 1H), 1.17 (d, J=6.1 Hz, 3H). $^{13}$C NMR (101 MHz, CDCl$_3$) δ 161.8 (d, J=245.7 Hz), 161.6 (d, J=245.4 Hz), 138.2 (d, J=3.3 Hz), 137.0 (d, J=3.3 Hz), 130.2 (d, J=7.8 Hz), 129.6 (d, J=7.9 Hz), 115.7 (d, J=21.2 Hz), 115.5 (d, J=21.0 Hz), 70.1, 58.6, 21.6. $^{19}$F NMR (376 MHz, CDCl3) δ −115.84, −116.16. ESIMS m/z 231.3 ([M-OH]+). Chiral HPLC analysis was performed using a Chiralpak IA column (250×4.6 mm, P/N: 80325) with isocratic 85% hexanes (0.1% trifluoroacetic acid) and 15% isopropanol (0.1% trifluoroacetic acid) mobile phase (10 μL injected). Using a UV detector set to 265 nm, enantiomer #1 (major) eluted at 6.2 minutes and enantiomer #2 (minor) eluted at 6.8 minutes. The enantiopurity was determined to be 98% ee.

Example 1r. (S)-1,1-bis(4-fluorophenyl)propan-2-ol

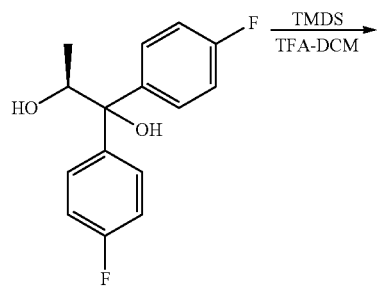

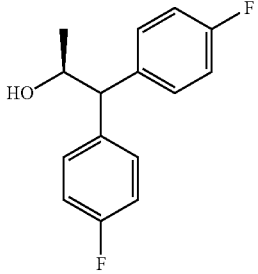

A 50 mL, three-neck round bottom flask equipped with a magnetic stirrer, a thermocouple and a nitrogen inlet was charged with (S)-1,1-bis(4-fluorophenyl)propane-1,2-diol (1.0 g, 3.8 mmol), CH$_2$Cl$_2$ (3 mL), and TMDS (2.0 mL, 1.1 mmol). TFA (5.8 mL, 7.6 mmol) was added dropwise. After 30 min, the reaction was complete by HPLC analysis. The reaction mixture was washed with a saturated aqueous solution of sodium carbonate (20 mL×2). The organic layer was dried over sodium sulfate, filtered and concentrated. The crude product was purified by column chromatography (SiO$_2$, 0-40% EtOAc in hexanes) to give a colorless oil (0.68 g, 75% yield). $^1$H NMR (400 MHz, CDCl$_3$) δ 7.38-7.29 (m, 2H), 7.25-7.16 (m, 2H), 7.07-6.89 (m, 4H), 4.51-4.43 (m, 1H), 3.80 (d, J=8.2 Hz, 1H), 1.53 (bs, 1H), 1.19 (d, J=6.1 Hz, 3H). $^{19}$F NMR (376 MHz, CDCl$_3$) δ −115.86, −116.20.

Example 1s. (S)-1,1-bis(4-fluorophenyl)propan-2-ol

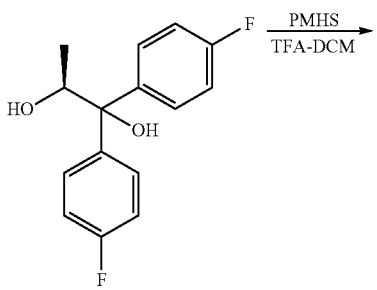

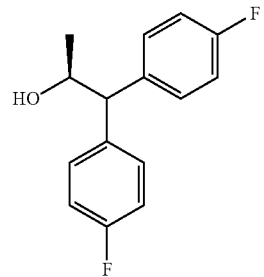

A 100 mL, three-neck, round bottom flask equipped with a magnetic stirrer, a thermocouple and a nitrogen inlet was charged with (S)-1,1-bis(4-fluorophenyl)propane-1,2-diol (1.23 g, 4.67 mmol), and CH$_2$Cl$_2$ (53 mL), and the resulting solution was cooled to 0° C. Neat PMHS (M$_N$=1700-3200, 2.9 g) was added followed by dropwise addition of neat TFA (5.4 g, 46.7 mmol). After 80 min, the reaction was quenched by addition to 50 mL of 1 M NaOH. CH$_2$Cl$_2$ (30 mL) was added. The aqueous layer was separated and extracted with additional CH$_2$Cl$_2$ (2×35 mL). The combined organics were washed with brine, dried (Na$_2$SO$_4$) and rotary evaporated.

The crude product was purified by column chromatography (SiO₂, 0-45% EtOAc in hexanes) to give a colorless oil (0.613 g, 53% yield). $^1$H NMR (400 MHz, CDCl₃) δ 7.38-7.29 (m, 2H), 7.25-7.16 (m, 2H), 7.07-6.89 (m, 4H), 4.51-4.43 (m, 1H), 3.80 (d, J=8.2 Hz, 1H), 1.53 (bs, 1H), 1.19 (d, J=6.1 Hz, 3H). $^{19}$F NMR (376 MHz, CDCl₃) δ -115.86, -116.20. Chiral HPLC analysis showed a single enantiomer.

Example 1t. (S,S)-1,1-bis(4-fluorophenyl)propan-2-yl 2-((tert-butoxycarbonyl)amino)propanoate

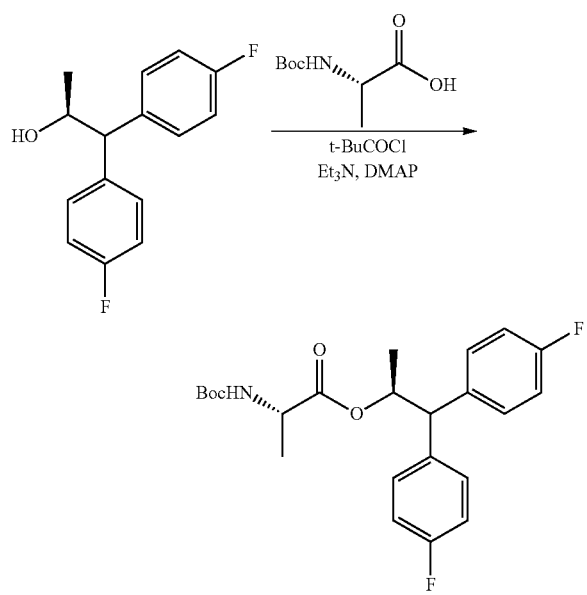

A 250 mL flask equipped with a stir bar was charged with (S)-2-((tert-butoxycarbonyl)amino)propanoic acid (0.91 g, 4.8 mmol) and DCM (20 mL) and cooled to 0° C. Triethylamine (1.4 mL, 10 mmol) was added to the reaction flask. As pivaloyl chloride (0.59 mL, 4.8 mmol) was slowly added to the reaction mixture a white precipitate began to form. After stirring for 15 min at 0° C., (S)-1,1-bis(4-fluorophenyl)propan-2-ol (993 mg, 4.0 mmol) was added, followed by N,N-dimethylpyridin-4-amine (49 mg, 0.4 mmol), and the reaction was stirred overnight at RT. The reaction was quenched with water, and the layers were separated. The aqueous layer was extracted once with DCM. The combined organic layers were dried with Na2SO4, filtered and concentrated to afford a colorless oil. The crude material was purified via silica gel chromatography by eluting with an ethyl acetate/hexane gradient to afford the title compound as a white foam (1.4 g, 83%): $^1$H NMR (300 MHz, CDCl₃) δ 7.29-7.17 (m, 4H), 7.03-6.92 (m, 4H), 5.71 (dq, J=9.8, 6.2 Hz, 1H), 4.94 (d, J=8.0 Hz, 1H), 4.12 (q, J=7.1 Hz, 1H), 4.02 (d, J=9.9 Hz, 1H), 1.42 (s, 9H), 1.22 (d, J=6.2 Hz, 3H), 0.84 (d, J=7.2 Hz, 3H); $^{13}$C NMR (126 MHz, CDCl₃) δ 172.8, 161.7 (d, J=246.1 Hz), 161.7 (d, J=245.6 Hz), 154.9, 137.0 (d, J=3.3 Hz), 136.8 (d, J=3.4 Hz), 129.5 (d, J=7.9 Hz), 129.5 (d, J=7.8 Hz), 115.7 (d, J=21.3 Hz), 115.4 (d, J=21.3 Hz), 79.8, 72.9, 56.2, 49.2, 28.3, 19.2, 18.1; $^{19}$F NMR (376 MHz, CDCl₃) δ -115.56, -115.97; ESIMS m/z 442.1 ([M+Na]⁺).

Example 1u. (S,S)-1,1-bis(4-fluorophenyl)propan-2-yl 2-aminopropanoate Hydrochloride

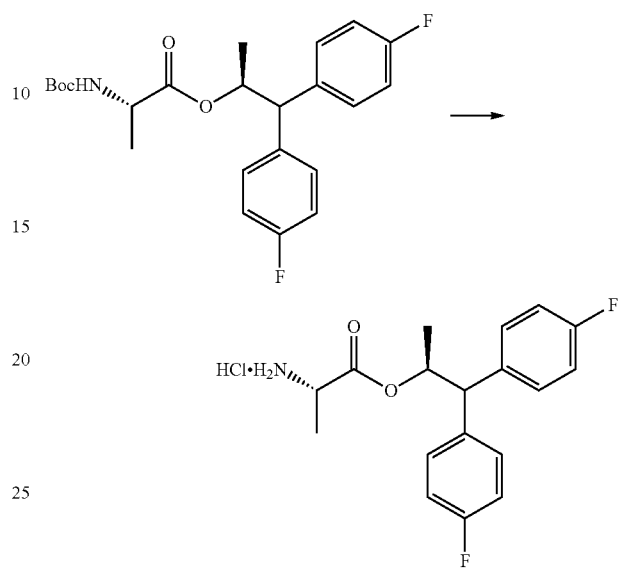

A 3 L single-neck flask equipped with a stir bar was charged with (S,S)-1,1-bis(4-fluorophenyl)propan-2-yl 2-((tert-butoxycarbonyl)amino)propanoate (130 g, 294 mmol) and dioxane (100 mL). HCl in dioxane (750 mL, 3 mol, 4M solution) was added to the stirring mixture at rtRT (20° C.). The reaction was stirred overnight and then concentrated in vacuo to yield a sticky, tan foam. Diethyl ether (1.75 L) was added and the heterogeneous mixture was vigorously stirred for 30 min. The mixture was filtered, rinsed with diethyl ether, followed by hexane and vacuum dried to afford a white solid (104.7 g, 100%): $^1$H NMR (300 MHz, DMSO-d₆) δ 8.38 (s, 3H), 7.56-7.40 (m, 4H), 7.18-7.10 (m, 4H), 5.77 (dq, J=12.2, 6.2 Hz, 1H), 4.27 (d, J=10.1 Hz, 1H), 3.91 (q, J=7.1 Hz, 1H), 1.17 (d, J=6.1 Hz, 3H), 0.81 (d, J=7.2 Hz, 3H); $^{13}$C NMR (101 MHz, DMSO-d₆) δ 169.5, 161.0 (d, J=243.2 Hz), 160.9 (d, J=242.7 Hz), 137.8 (d, J=3.2 Hz), 137.3 (d, J=3.2 Hz), 130.0 (d, J=7.9 Hz), 129.8 (d, J=7.9 Hz), 115.4 (d, J=21.1 Hz), 115.2 (d, J=21.0 Hz), 73.7, 54.7, 47.6, 18.8, 15.0; $^{19}$F NMR (376 MHz, DMSO-d₆) δ -115.89, -116.29; ESIMS m/z 320.1 ([M+H]⁺).

Example 1v. (S)-1,1-bis(4-fluorophenyl)propane-1,2-diol

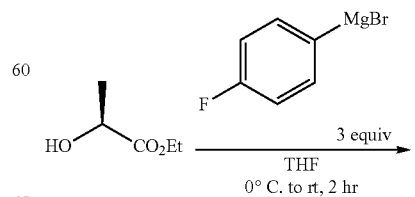

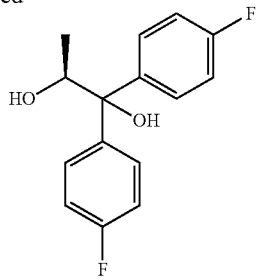

A 5 L, 3-neck flask, equipped with overhead stirring, internal temperature probe, addition funnel and nitrogen atmosphere, was charged with (4-fluorophenyl)magnesium bromide (1600 mL, 1600 mmol, 1M in THF). The mixture was cooled to 0° C. and a solution of (S)-ethyl lactate (60 g, 483 mmol) in THF (500 ml) was slowly added via addition funnel (40 min) and the temperature of the reaction never rose above 0° C. While still cold (4° C.), the reaction was quenched with sat. aq. NH4Cl (250 mL) and stirred until the reaction reached ambient temperature. The liquid layer was decanted off from the white solid. The white solid was suspended in EtOAc, filtered and rinsed with EtOAc. The combined organic phases were concentrated under vacuum. The residue was taken up in EtOAc, transferred to a separatory funnel, and washed with water. The organic phase was dried over Na2SO4, filtered and concentrated under vacuum to yield a yellow oil. The crude material was taken up in acetonitrile (500 mL) and extracted with hexane (2×300 mL). The acetonitrile layer was dried over $Na_2SO_4$, filtered and concentrated to yield 117 g of a yellow oil. The crude material was chromatographed on a 1.5 kg ISCO silica gel cartridge, eluting with an EtOAc/hexane gradient to afford 88.3 g of white solid (66%). $^1$H NMR (400 MHz, Chloroform-d) δ 7.59-7.49 (m, 2H), 7.41-7.32 (m, 2H), 7.07-6.92 (m, 4H), 4.74 (qd, J=6.2, 3.8 Hz, 1H), 3.00 (s, 1H), 1.81 (d, J=3.8 Hz, 1H), 1.08 (d, J=6.3 Hz, 3H). 13C NMR (101 MHz, CDCl3) δ 161.9 (d, J=246.8 Hz), 161.7 (d, J=246.0 Hz), 141.2 (d, J=3.3 Hz), 139.6 (d, J=3.2 Hz), 128.1 (d, J=7.9 Hz), 127.4 (d, J=8.0 Hz), 115.4 (d, J=21.3 Hz), 115.0 (d, J=21.3 Hz), 79.3, 71.5, 16.9. $^{19}$F NMR (376 MHz, CDCl$_3$) δ -115.3, -115.9. ESIMS m/z 263.1 ([M-H]-).

Example 1w.
(S)-1,1-bis(4-fluorophenyl)propane-1,2-diol

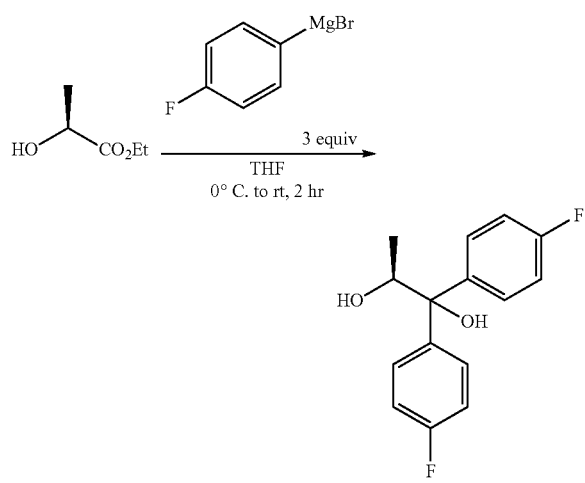

Magnesium turnings (12.6 kg, 3.5 eq) and anhydrous tetrahydrofuran (115.6 L) were charged into a stainless steel reactor with stirring under nitrogen atmosphere at 25-30° C. The reaction mixture was heated to 40-45° C. A solution of 4-bromofluorobenzene in tetrahydrofuran (81.35 kg, 3.25 eq of 4-bromofluorobenzene in 115.6 L of THF) was added dropwise at 50-55° C. and maintained for 30 min. The reaction mixture was allowed to cool to 0-3° C., and then a solution of ethyl L-lactate in tetrahydrofuran (17.0 Kg, 1.0 eq of ethyl L-lactate in 84.2 L of THF) was added dropwise at 0-3° C. over a period of 2.0 h and maintained for 30 min. A saturated solution of ammonium chloride (119.0 L, 41.65 kg ammonium chloride in 119.0 L water) was added dropwise at 0-10° C. over a period of 2.0 h. The reaction mixture was filtered, and the solid was washed with ethyl acetate (3×125.8 L). The filtrate was charged back to the reactor and washed with brine solution (1×85.0 L, 5.0 vol). The aqueous layer was re-extracted with ethyl acetate (1×125.8 L, 7.4 volume), the combined organic layers were washed with brine (1×85.0 L, 5.0 volume), dried over sodium sulphate (8.5 kg, 0.5 volume), filtered and concentrated completely at 40-45° C. under vacuum (500-600 mm Hg) to give a pale yellow oil. Hexanes (85.0 L, 5.0 volume) were added, and concentrated below 45° C. under vacuum (500-600 mm Hg) until no distillate was observed. Added hexanes (119.0 L), stirred for 15 min, cooled to 8-12° C. and maintained for 1 h. The solids were filtered and washed with hexanes (1×17.0 L). The above wet solid was charged back to the reactor, 2% MTBE in hexanes (119.0 L, 7.0 volume) were added and stirred at 25-30° C. for 30 min. Filtered the mass, washed with hexanes (51.0 L) and dried the solid at 35-40° C. under vacuum (500-600 mm Hg) to give (S)-1,1-bis(4-fluorophenyl)propane-1,2-diol as a pale yellow powder (26.0 kg, 68.3% yield). HPLC (Hypersil BDS C18, (250×4.6) mm, 5.0 μm; A: 0.1% TFA in water, B: ACN, Flow: 1.0 mL/min) showed the product to be 95.1% pure.

Example 1x. 3-(Acetyloxy)-4-methoxypicolinic Acid

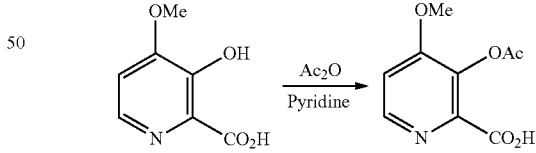

3-Hydroxy-4-methoxypicolinic acid (5.0 g, 29.6 mmol) was slurried in 50 mL of pyridine and 50 mL of acetic anhydride at ambient temperature. After 1 h, a yellow solution had formed which was then stirred overnight. The solution was evaporated at 45° C. (2 mm Hg) to give 6.28 g of tan solid (99% yield, mp=132-134° C.). $^1$H NMR (400 MHz, DMSO-d$_6$) δ 13.32 (s, 1H), 8.43 (d, J=5.5 Hz, 1H), 7.40 (d, J=5.5 Hz, 1H), 3.91 (s, 3H), 2.27 (s, 3H). $^{13}$C NMR (101 MHz, DMSO-d$_6$) δ 167.95, 164.81, 158.34, 147.87, 142.77, 136.18, 110.87, 56.59, 20.27. HRMS (m/z) calcd for $C_9H_9NO_5$ 211.0478, found 211.0481 ([M]$^+$).

Example 1y. 3-(Acetyloxy)-4-methoxypicolinic Acid

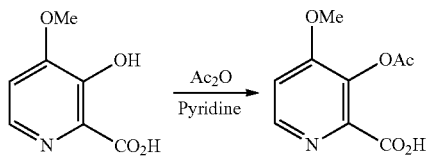

Pyridine (5.7 L, 1.0 volume), 3-hydroxy-4-methoxypicolinic acid (5.7 kg, 1.0 eq) and acetic anhydride (15.73 L, 5.0 eq) were charged into a glass-lined reactor with stirring under nitrogen atmosphere at 25-30° C. The above reaction mass was stirred at 25-30° C. for 18 h. After completion of the reaction, 30% MTBE in hexanes (28.5 L, 5.0 volume, 8.55 L MTBE in 19.95 L hexanes) was added, and the mixture was stirred at 25-30° C. for 2 h. The solid was filtered, washed with 20% MTBE in hexanes (34.2 L, 6.0 volume, 6.8 L MTBE in 27.4 L hexanes) and allowed to dry. The solid was dried at 25-30° C. under vacuum (500-600 mm Hg) to give 3-(acetyloxy)-4-methoxypicolinic acid as a pale yellow powder (6.85 kg, 96.3% yield). HPLC (Zorbax SB-Aq, (250×4.6) mm, 5.0 μm; A: 0.1% TFA in water, B: Acetonitrile, Flow: 1.0 mL/min) showed the product to be 98.5% pure.

Example 1z. (S,S)-1,1-bis(4-fluorophenyl)-propan-2-yl 2-(3-acetoxy-4-methoxypicolinamido)propanoate

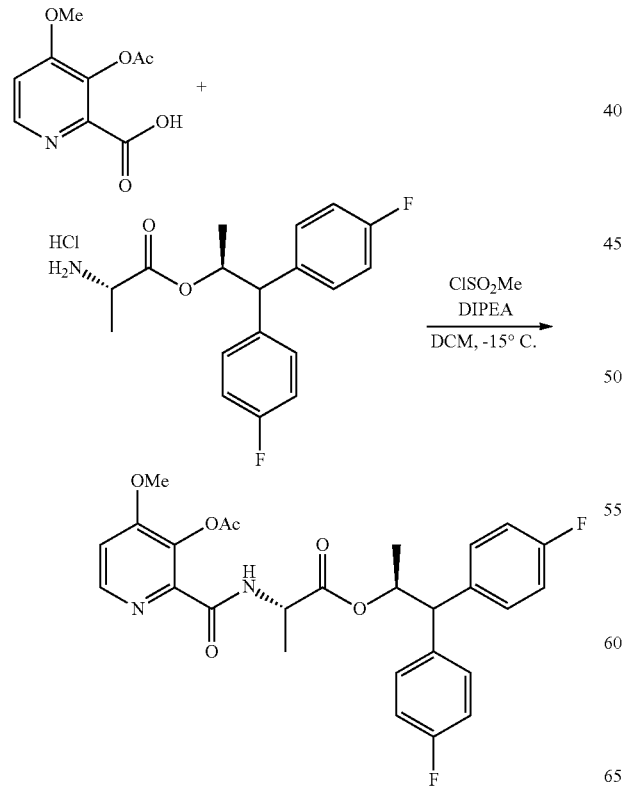

A flask equipped with a stir bar and nitrogen inlet was charged with 3-acetoxy-4-methoxypicolinic acid (2.97 g, 14.05 mmol) and DCM (28.1 mL). DIPEA (9.82 mL, 56.2 mmol) was added and the reaction was cooled to −15° C. Methanesulfonyl chloride (1.095 mL, 14.05 mmol) was then slowly added. After stirring for 15 minutes, (S)-1,1-bis(4-fluorophenyl)propan-2-yl L-alaninate hydrochloride (5 g, 14.05 mmol) was added. After 90 minutes of stirring, the mixture was allowed to warm. The solution was poured into saturated NH$_4$Cl(aq) in a separatory funnel. The layers were separated, and the organic layer was washed with 1:1 brine/1N HCl then with water. The DCM layer was dried over Na$_2$SO$_4$, filtered and concentrated to provide an oil. The crude material was purified via silica gel chromatography by eluting with an ethyl acetate/hexane gradient to afford the title compound as a white foam (2.9 g, 38% yield): $^1$H NMR (400 MHz, CDCl$_3$) δ 8.39 (s, 1H), 8.32 (d, J=5.4 Hz, 1H), 7.26-7.16 (m, 4H), 7.03-6.87 (m, 5H), 5.71 (dq, J=9.6, 6.1 Hz, 1H), 4.55 (dd, J=8.0, 7.1 Hz, 1H), 4.04 (d, J=9.6 Hz, 1H), 3.91 (s, 3H), 2.38 (s, 3H), 1.22 (d, J=6.1 Hz, 3H), 0.99 (d, J=7.2 Hz, 3H); $^{19}$F NMR (376 MHz, CDCl$_3$) δ −115.61, −115.96; HRMS-ESI (m/z) [M+H]$^+$ calcd for C$_{27}$H$_{27}$F$_2$N$_2$O$_6$, 512.1759; found, 513.1825.

What is claimed is:

1. A process for the preparation of the compound of Formula A

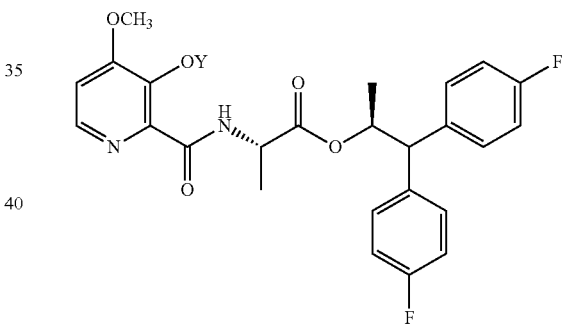

wherein Y is CH$_3$CO;

from the compound of Formula B

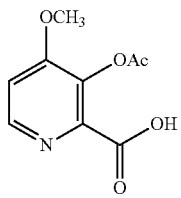

which comprises the following steps:
- a) creating a first mixture containing the compound of Formula B, an acylating agent or a chlorinating agent, and a base;
- b) adding at least one of the compounds of Formula C and Formula J

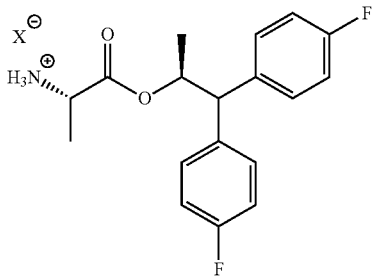

C wherein X is Cl, Br, HSO$_4$, H$_2$PO$_4$ or CH$_3$SO$_3$ and

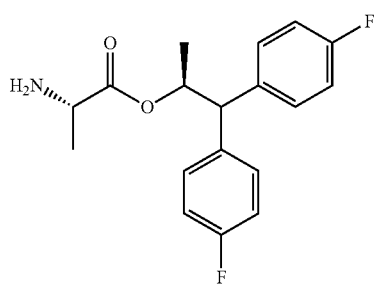

J to the first mixture to form a second mixture; and
c) isolating the compound of Formula A from the second mixture.

2. The process of claim 1 wherein the acylating agent is an alkyl chloroformate of the Formula ClCO$_2$R, wherein R is a C$_1$-C$_4$ alkyl or benzyl, or an acid chloride of the Formula RCOCl, wherein R is a C$_1$-C$_4$ alkyl.

3. The process of claim 1 wherein the chlorinating agent is oxalyl chloride or thionyl chloride.

4. The process of claim 1 wherein the base may be selected from the group including triethylamine (TEA), diisopropylethylamine (DIPEA), pyridine, potassium carbonate, and mixtures thereof.

5. The process of claim 1 wherein the first mixture further comprises a solvent selected from the group including dichloromethane (DCM), 1,2-dichloroethane (DCE), isopropyl acetate, tetrahydrofuran (THF), 2-MeTHF, acetonitrile (ACN), and mixtures thereof.

6. A process for the preparation of the compound of Formula A

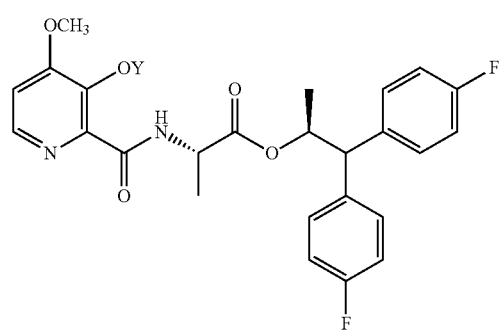

A wherein Y is CH$_3$CO or CH$_3$COOCH$_2$, which comprises the following steps:
a) creating a first mixture containing the compound of Formula D,

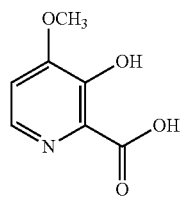

D an acylating agent, and a first base;
b) adding at least one of the compounds of Formula C and Formula J

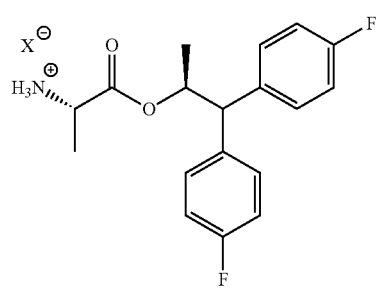

C wherein X is Cl, Br, HSO$_4$, H$_2$PO$_4$ or CH$_3$SO$_3$ and

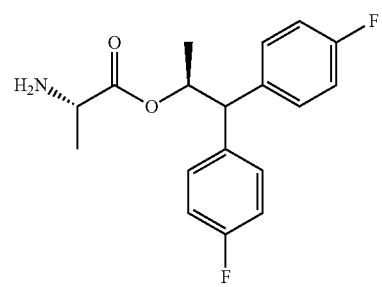

J to the first mixture to form a second mixture; and
c) isolating the compound of Formula E from the second mixture;

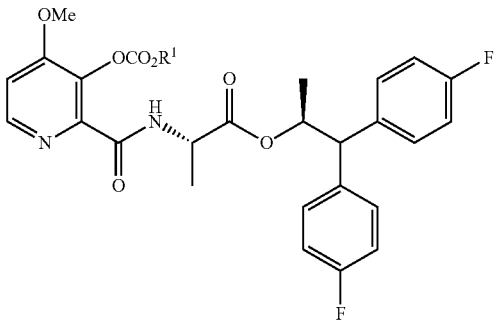

E wherein R¹ is a $C_1$-$C_4$ alkyl or a benzyl;
d) creating a third mixture containing the compound of Formula E, an alkali metal base and water;
e) isolating the compound of Formula F from the third mixture;

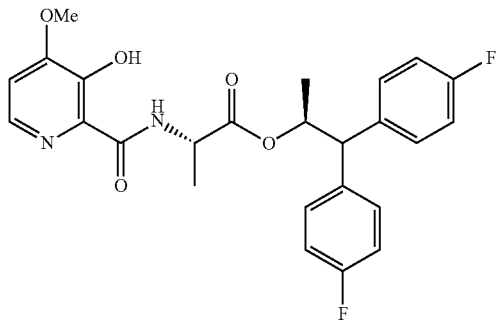

F f) creating a fourth mixture containing the compound of Formula F, an acetylating agent or an alkylating agent, and a second base; and
g) isolating the compound of Formula A from the fourth mixture.

7. The process of claim 6 wherein the acylating agent is an alkyl chloroformate of the Formula $ClCO_2R$, wherein R is a $C_1$-$C_4$ alkyl or a benzyl.

8. The process of claim 6 wherein the first mixture further comprises a solvent selected from the group including dichloromethane (DCM), 1,2-dichloroethane (DCE), acetonitrile (ACN), isopropyl acetate, THF, 2-MeTHF, and mixtures thereof.

9. The process of claim 6 wherein the first base may be selected from the group including triethylamine (TEA), diisopropylethylamine (DIPEA), pyridine and potassium carbonate.

10. The process of claim 6 wherein about 3 equivalents of the first base and about 2 equivalents of the acylating agent are used.

11. The process of claim 6 wherein the alkali metal base may be selected from the group including LiOH, NaOH, KOH, and mixtures thereof.

12. The process of claim 6 wherein the third mixture further comprises a co-solvent selected from the group including THF, 2-MeTHF, DME, dioxane, ACN and a $C_1$-$C_4$ alcohol.

13. The process of claim 6 wherein the acetylating agent may be selected from acetic anhydride and acetyl chloride.

14. The process of claim 6 wherein the alkylating agent is $CH_3COOCH_2Br$.

15. The process of claim 6 wherein the second base may be selected from the group including pyridine, TEA, DIPEA, and mixtures thereof.

* * * * *